US010870630B2

(12) United States Patent
Crowley et al.

(10) Patent No.: US 10,870,630 B2
(45) Date of Patent: Dec. 22, 2020

(54) SUBSTITUTED BICYCLIC HETEROARYL ALLOSTERIC MODULATORS OF NICOTINIC ACETYLCHOLINE RECEPTORS

(71) Applicant: Merck Sharp & Dohme Corp., Rahway, NJ (US)

(72) Inventors: Brendan M. Crowley, Collegeville, PA (US); Ian M. Bell, Harleysville, PA (US); Andrew John Harvey, Paddington (AU); William D. Shipe, Chalfont, PA (US); Kenneth J. Leavitt, Mount Laurel, NJ (US); John M. Sanders, Hatfield, PA (US); Deodial G. Guiadeen, Chesterfield, NJ (US); Linda M. Suen, Philadelphia, PA (US); Thomas J. Greshock, Collegeville, PA (US); Vanessa L. Rada, Hatfield, PA (US)

(73) Assignee: Merck Sharp & Dohme Corp.

( * ) Notice: Subject to any disclaimer, the term of this patent is extended or adjusted under 35 U.S.C. 154(b) by 42 days.

(21) Appl. No.: 16/345,903

(22) PCT Filed: Oct. 30, 2017

(86) PCT No.: PCT/US2017/058933
§ 371 (c)(1),
(2) Date: Apr. 29, 2019

(87) PCT Pub. No.: WO2018/085171
PCT Pub. Date: May 11, 2018

(65) Prior Publication Data
US 2019/0308945 A1    Oct. 10, 2019

Related U.S. Application Data

(60) Provisional application No. 62/558,606, filed on Sep. 14, 2017, provisional application No. 62/415,788, filed on Nov. 1, 2016.

(51) Int. Cl.

| | |
|---|---|
| *C07D 263/56* | (2006.01) |
| *A61K 31/498* | (2006.01) |
| *C07D 239/74* | (2006.01) |
| *C07D 241/42* | (2006.01) |
| *C07D 265/16* | (2006.01) |
| *C07D 277/68* | (2006.01) |
| *C07D 471/04* | (2006.01) |
| *C07D 487/04* | (2006.01) |

(Continued)

(52) U.S. Cl.
CPC .......... *C07D 263/56* (2013.01); *A61K 31/416* (2013.01); *A61K 31/4162* (2013.01); *A61K 31/423* (2013.01); *A61K 31/428* (2013.01); *A61K 31/437* (2013.01); *A61K 31/4365* (2013.01); *A61K 31/4375* (2013.01); *A61K 31/498* (2013.01); *A61K 31/502* (2013.01); *A61K 31/5025* (2013.01); *A61K 31/517* (2013.01); *A61K 31/536* (2013.01); *A61K 31/5383* (2013.01); *A61K 45/06* (2013.01); *C07C 311/08* (2013.01); *C07D 217/02* (2013.01); *C07D 231/56* (2013.01); *C07D 235/06* (2013.01); *C07D 237/28* (2013.01); *C07D 239/74* (2013.01); *C07D 241/42* (2013.01); *C07D 263/52* (2013.01); *C07D 265/16* (2013.01); *C07D 265/36* (2013.01); *C07D 277/66* (2013.01); *C07D 277/68* (2013.01); *C07D 471/04* (2013.01); *C07D 487/02* (2013.01); *C07D 487/04* (2013.01); *C07D 491/048* (2013.01); *C07D 495/04* (2013.01); *C07D 498/04* (2013.01)

(58) Field of Classification Search
CPC .............................. C07D 263/56; A61P 31/498
See application file for complete search history.

(56) References Cited

U.S. PATENT DOCUMENTS

| | | | | |
|---|---|---|---|---|
| 9,840,481 B2 * | 12/2017 | Crowley | ............... | A61K 31/415 |
| 9,926,285 B2 * | 3/2018 | Crowley | ............... | A61K 31/415 |

FOREIGN PATENT DOCUMENTS

| | | |
|---|---|---|
| WO | 200222602 A2 | 3/2002 |
| WO | 2007130780 A2 | 11/2007 |

(Continued)

OTHER PUBLICATIONS

International Search Report and Written Opinion for PCT/US2017/058933, dated Oct. 30, 2017; 9 pages.

*Primary Examiner* — Golam M Shameem
(74) *Attorney, Agent, or Firm* — Patricia A. Shatynski; John C. Todaro

(57) ABSTRACT

The present disclosure relates to compounds of formula (I) that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia, as well as for L-DOPA induced-dyskinesia and inflammation.

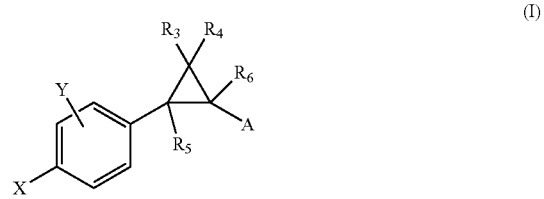

13 Claims, No Drawings

(51) Int. Cl.
*C07D 498/04* (2006.01)
*A61K 31/4375* (2006.01)
*A61K 31/5383* (2006.01)
*A61K 31/416* (2006.01)
*A61K 31/428* (2006.01)
*A61K 31/4365* (2006.01)
*A61K 31/502* (2006.01)
*A61K 31/4162* (2006.01)
*A61K 45/06* (2006.01)
*C07D 231/56* (2006.01)
*A61K 31/536* (2006.01)
*A61K 31/423* (2006.01)
*C07D 217/02* (2006.01)
*A61K 31/5025* (2006.01)
*A61K 31/517* (2006.01)
*C07D 237/28* (2006.01)
*C07D 495/04* (2006.01)
*C07C 311/08* (2006.01)
*A61K 31/437* (2006.01)
*C07D 491/048* (2006.01)
*C07D 487/02* (2006.01)
*C07D 277/66* (2006.01)
*C07D 265/36* (2006.01)
*C07D 235/06* (2006.01)
*C07D 263/52* (2006.01)

(56) References Cited

FOREIGN PATENT DOCUMENTS

| WO | 2009043784 | 4/2009 |
| WO | 2010122082 A1 | 10/2010 |
| WO | WO2014019023 | 2/2014 |
| WO | WO2015191799 | 12/2015 |

* cited by examiner

SUBSTITUTED BICYCLIC HETEROARYL ALLOSTERIC MODULATORS OF NICOTINIC ACETYLCHOLINE RECEPTORS

CROSS REFERENCE TO RELATED APPLICATIONS

This application is a U.S. National Phase application under 35 U.S.C. § 371 of PCT Application No. PCT/US2017/058933, filed Oct. 30, 2017 which claims priority under 35 U.S.C. § 119(e) from U.S. Provisional Application Ser. No. 62/415,788, filed on Nov. 1, 2016 and U.S. Provisional Application Ser. No. 62/558,606, filed on Sep. 14, 2017.

FIELD OF THE INVENTION

The present disclosure relates to compounds that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia.

BACKGROUND OF THE INVENTION

The α7 nAChR is a fast desensitizing ligand-gated ion channel that has high permeability to $Ca^{2+}$. In human brain, α7 nAChRs are highly expressed in the cortex and hippocampus, regions associated with cognition, see for example, Breese et al. *J. Comp. Neurol.* (1997) 387:385-398. In neurons, α7 nAChRs are localized in both pre-synaptic and post-synaptic structures, where activation of the receptor can modulate neurotransmitter release, neuronal excitability, and intracellular signalling, see for example, Frazier et al. *J Neurosci.* (1998) 18:1187-1195.

Cognitive impairments are prevalent in many neurological and psychiatric diseases, including Alzheimer's disease (AD), schizophrenia, and Parkinson's disease, and dysfunction in cholinergic signalling contributes to the cognitive impairments of these diseases, see for example, Francis et al. *J. Neurol. Neurosurg. Psychiatry* (1999) 66:137-147. For example, a principal feature of the pathogenesis in AD is the loss of cholinergic neurons in the basal forebrain nuclei, whereas increasing cholinergic transmission via inhibition of acetylcholine esterase is the standard of care for the cognitive symptoms of AD. More specific to the α7 nAChR, it was recently demonstrated that encenicline, a partial agonist of the α7 nAChR, improves cognition in Alzheimer's disease, see for example, Moebius H et al., 67th *Annual Meeting. Am. Acad. Neurol.* (AAN) 2015, Abst P7.100. Evidence implicating α7 nAChRs in the etiology of schizophrenia comes from studies demonstrating reduced expression of neuronal α7 nAChRs in the brain of schizophrenic patients and the observation that schizophrenics frequently smoke, which is believed to be a form of self-medication. In addition, variants in the promotor region of the gene coding for the α7 nAChR, CHRNA7, which impacts expression of the α7 nAChR protein, are associated with symptoms of schizophrenia, see for example, Sinkus et al. *Neuropharmacology* (2015) 96:274-288. Moreover, accumulating evidence from clinical trials has indicated that activating α7 nAChR with agonists may have beneficial effects on cognition, see for example, Keefe et al. *Neuropsychopharmacology* (2015) 40:3053-3060 and Bertrand et al. *Pharmacology Reviews* (2015) 67:1025-1073. Therefore, targeting the α7 nAChR represents a therapeutic strategy for the treatment of cognitive impairments associated with various cognitive disorders.

Parkinson's disease (PD) is a neurodegenerative disease characterized by progressive deficits in motor function, such as tremor, bradykinesia, rigidity and impaired postural reflex. The main pathological finding associated with the disease is degeneration of dopaminergic neurons in the substantia nigra, resulting in loss of dopaminergic tone in the striatum. L-DOPA is the current standard treatment for the motor symptoms in PD. However, chronic treatment with L-DOPA in PD patients also induces dyskinesia, a side effect of L-DOPA therapy. New lines of evidence indicate that activating α7 nAChRs acutely alleviates dyskinesia in several animal models, see for example, Zhang et al. *J. Pharmacol. Exp. Ther.* (2014) 351:25-32. In addition, accumulating evidence shows that pretreatment with α7 nAChR agonists may protect against neurodegeneration in nigrostriatal neurons, suggesting α7 activation may have disease modifying properties too, see for example, Suzuki et al. *J. Neurosci. Res.* (2013) 91:462-471. Overall, α7 nAChR is an attractive target for both ameliorating disease progression and managing dyskinesia.

In addition to its expression in the central nervous system, the α7 nAChR is widely expressed in peripheral immune cells including macrophage, monocytes, dendritic cells, and B and T cells, see for example, Rosas-Ballina et al. *Science* (2011) 334:98-101. Activation of peripheral α7 nAChRs is critical for inhibiting the release of proinflammatory cytokines via the cholinergic anti-inflammatory pathway, see for example, Wang et al. *Nature* (2003) 421:384-388. Therefore, α7 nAChR is a potential target for several inflammatory diseases such as rheumatoid arthritis, and atherosclerosis, see for example, de Jonge et al. *British J. Pharmacol.* (2007) 151:915-929.

In recent years, α7-selective positive allosteric modulators (PAMs) have been proposed as a therapeutic approach to treating cognitive impairments in AD, PD, and schizophrenia, as well as L-DOPA induced-dyskinesia and inflammation. In contrast to α7 agonists that activate the channel irrespective of endogenous agonist, PAMs increase the potency of the endogenous agonist without perturbing the temporal and spatial integrity of neurotransmission. There are two classs of α7 PAMs, type I and type II, which differ based on the functional properties of modulation. The type I PAMs (e.g. NS1738, see for example, Timmermann et al. *J. Pharmacol. Exp. Ther.* (2007) 323:294-307) predominantly affect the peak current with little or no effect on receptor desensitization, while the type II PAMs (e.g. PNU120596, see for example, Hurst et al. *J. Neurosci.* (2005) 25:4396-4405) markedly delay desensitization of the receptor. Additionally, α7 nAChR PAMs may have improved selectivity over related channel targets, presumably through binding to non-conserved regions of the receptor.

The present invention is directed to a new class of compounds that exhibit positive allosteric modulation of the α7 nAChR.

SUMMARY OF THE INVENTION

The present disclosure relates to novel compounds of formula I and pharmaceutically acceptable salts thereof. These compounds may be useful, either as compounds or their pharmaceutically acceptable salts (when appropriate), in the modulation of the α7 nAChR, the prevention, treatment, or amelioration of disease, particularly disorders of the central nervous system such as cognitive impairments in Alzheimer's disease, Parkinson's disease, and schizophrenia and/or as pharmaceutical composition ingredients. As pharmaceutical composition ingredients, these compounds and their salts may be the primary active therapeutic agent, and, when appropriate, may be combined with other therapeutic agents including but not limited to acetylcholinesterase inhibitors, NMDA receptor antagonists, beta-secretase inhibitors, M4 mAChR agonists or PAMs, mGluR2 antagonists or NAMs or PAMs, 5-HT6 antagonists, histamine H3 receptor antagonists, PDE4 inhibitors, PDE9 inhibitors, HDAC6 inhibitors, antipsychotics, MAO-B inhibitors, and levodopa.

In one aspect, the present invention relates to a compound of formula I:

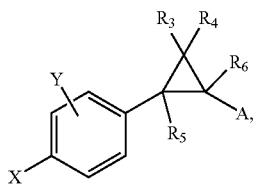

(I)

or a pharmaceutically acceptable salt thereof, wherein:
X is selected from

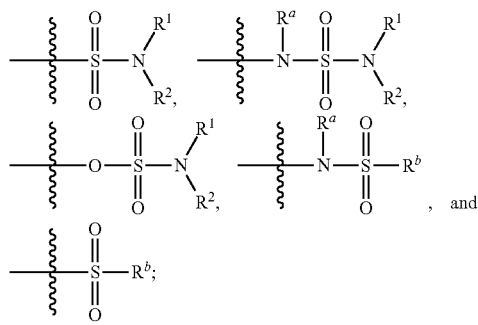

Y is 4 substituents, each independently selected from H, $(C_1-C_4)$alkyl, halogen, and OH, wherein said alkyl is optionally substituted with one or more halogen or OH;

A is a bicyclic heteroaryl ring which is substituted with 0 to 4 R groups each independently selected from OH, oxo, amino, amido, carboxyl, keto, CN, alkoxy, $S(O)_m$-alkyl, halogen, aminoalkyl, hydroxyalkyl, alkyl, cycloalkyl, alkynyl, aryl, heteroaryl, and heterocyclyl, wherein said amino, amido, carboxyl, keto, alkoxy, $S(O)_m$-alkyl, aminoalkyl, hydroxyalkyl, alkyl, cycloalkyl, alkynyl, aryl, heteroaryl and heterocyclyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(O)_m$—$(C_1-C_4)$alkyl, C=O$(C_1-C_4)$alkyl, (C=O)$NR^7R^8$, (C=O)$OR^7$, $(C_2-C_4)$alkynyl, $(C_3-C_6)$cycloalkyl, O$(C_3-C_6)$cycloalkyl, C=O$(C_3-C_6)$cycloalkyl, aryl, heteroaryl and heterocyclyl, wherein said alkyl, aryl, heteroaryl and heterocyclyl are optionally independently substituted with one or more halogen, $CF_3$, OH and oxo;

$R^1$ is H or $(C_1-C_4)$alkyl;
$R^2$ is H or $(C_1-C_4)$alkyl;
$R^3$ is H, halogen or $(C_1-C_4)$alkyl, wherein said alkyl is optionally substituted with one or more halogen;

$R^4$ is H, halogen or $(C_1-C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl;
$R^5$ is H or $(C_1-C_4)$alkyl;
$R^6$ is H or $(C_1-C_4)$alkyl;
$R^7$ is H or $(C_1-C_4)$alkyl, wherein said alkyl is optionally substituted with one or more halogen;
$R^8$ is H or $(C_1-C_4)$alkyl, wherein said alkyl is optionally substituted with one or more halogen;
$R^a$ is H or $(C_1-C_4)$alkyl;
$R^b$ is H or $(C_1-C_4)$alkyl; and
m is 0, 1, or 2.

The present invention also includes pharmaceutical compositions containing a compound of the present invention and methods of preparing such pharmaceutical compositions. The present invention further includes methods of preventing, treating, or ameliorating the cognitive impairments associated with Alzheimer's disease, Parkinson's disease, and schizophrenia.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are positive allosteric modulators of α7 nAChR.

In a first embodiment of the invention, X is

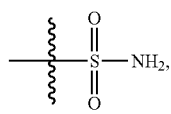 [SMILES: *S(N)(=O)=O]

and the other groups are as provided in the general formula above.

In a second embodiment of the invention, Y is H and the other groups are as provided in the general formula above, or as in the first embodiment.

In a third embodiment of the invention, A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl, dihydropyridooxazinyl, tetrahydrobenzothiazolyl, tetrahydroquinazolinyl, benzoxazinyl, benzimidazolyl, thiazolopyridinyl, quinolinyl, pyridopyrimidinyl, phthalazinyl, pyridopyrazinyl, thienoxazole, and thienothiazole each optionally substituted with 1 to 2 R groups independently selected from halogen, CN, $(C_1-C_6)$alkyl, $O(C_1-C_4)$alkyl, $NR^7R^8$, $(C_3-C_6)$cycloalkyl, aryl, heteroaryl and heterocyclyl, wherein said alkyl, $NR^7R^8$, $(C_3-C_6)$cycloalkyl, aryl, heteroaryl and heterocyclyl are each optionally substituted with one or more substituents independently selected from halogen, CN, $(C_1-C_6)$alkyl, (C=O)O$(C_1-C_4)$alkyl, and phenyl; and the other groups are as provided in the general formula above, or as in the first or second embodiment.

In a fourth embodiment of the invention, $R^5$, $R^6$, $R^a$ and $R^b$ are independently H or methyl, and the other groups are as provided in the general formula above, or as in the first, second, or third embodiments.

In a fifth embodiment of the invention, $R^3$ and $R^4$ are independently H, F or methyl, and the other groups are as provided in the general formula above, or as in the first through fourth embodiments.

In a sixth embodiment of the invention, the compound of the invention has the formula:

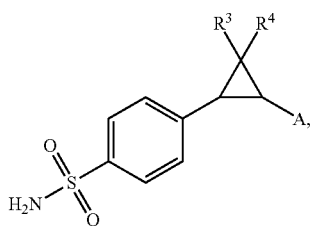

(Ia)

or a pharmaceutically acceptable salt thereof, wherein;

A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl and dihydropyridooxazinyl each optionally substituted with 1 to 2 R groups independently selected from F, Cl, $(C_1-C_4)$alkyl, $O(C_1-C_4)$alkyl and $CF_3$;

$R^3$ is H, F or methyl; and
$R^4$ is H, F or methyl.

The invention is also directed to a compound, or a pharmaceutically acceptable salt thereof, selected from the following exemplified compounds:

4-[(1R,3R)-3-(1,3-Benzoxazol-2-yl)-2,2-dimethylcyclopropyl]benzenesulfonamide;
4-[(1S,3S)-3-(6-Fluoro-1,3-benzoxazol-2-yl)-2,2-dimethylcyclopropyl]benzenesulfonamide;
4-[(1R,2R)-2-(Quinazolin-2-yl)cyclopropyl]benzenesulfonamide;
4-[(1R,2R)-2-(4,5,6,7-Tetrahydro-1,3-benzoxazol-2-yl)cyclopropyl]benzenesulfonamide;
4-[(1R,2R)-2-(1,3-Benzoxazol-2-yl)cyclopropyl]benzenesulfonamide;
4-[(1R,3R)-2,2-Dimethyl-3-([1,3]oxazolo[5,4-b]pyridin-2-yl)cyclopropyl]benzenesulfonamide;
4-[trans-2-(Quinoxalin-2-yl)cyclopropyl]benzenesulfonamide;
4-((1R,3R)-3-(Imidazo[1,2-b]pyridazin-2-yl)-2,2-dimethylcyclopropyl)benzenesulfonamide;
4-((1S,3S)-3-(Benzo[d]thiazol-2-yl)-2,2-dimethylcyclopropyl)benzenesulfonamide;
4-((1S,3S)-3-(6-Fluorobenzo[d]thiazol-2-yl)-2,2-dimethylcyclopropyl)benzenesulfonamide;
4-[(1R,3R)-3-(5,6-Dihydro-4H-cyclopenta[d][1,3]oxazol-2-yl)-2,2-dimethylcyclopropyl]benzenesulfonamide;
4-[(1R,3R)-2,2-Dimethyl-3-(5,6,7,8-tetrahydroquinazolin-2-yl)cyclopropyl]benzenesulfonamide;
4-[(1R,3R)-3-(4,4-Dimethyl-4H-3,1-benzoxazin-2-yl)-2,2-difluorocyclopropyl]benzenesulfonamide;
4-[(1S,3S)-3-(4-Methoxy-1,3-benzoxazol-2-yl)-2,2-dimethyl-cyclopropyl]benzenesulfonamide;

4-[(1R,2R)-2-(6-Fluoro-1,3-benzoxazol-2-yl)cyclopropyl]benzenesulfonamide;
4-[(1S,3S)-3-(4,6-Difluoro-1,3-benzothiazol-2-yl)-2,2-dimethyl-cyclopropyl]benzenesulfonamide;
4-[(1S,3S)-3-(1,3-Benzoxazol-2-yl)-2,2-dimethyl-cyclopropyl]benzenesulfonamide;
4-[(1S,3S)-3-(6-Chloro-1,3-benzoxazol-2-yl)-2,2-dimethyl-cyclopropyl]benzenesulfonamide;
4-[(1S,3S)-3-(5-Chloro-1,3-benzoxazol-2-yl)-2,2-dimethyl-cyclopropyl]benzenesulfonamide;
4-[(1R,3R)-3-(1,3-Benzoxazol-2-yl)-2,2-difluoro-cyclopropyl]benzenesulfonamide;
4-[(1R,3S)-3-(1,3-Benzothiazol-2-yl)-2,2-difluoro-cyclopropyl]benzenesulfonamide;
4-[(1R,3R)-3-(1H-Benzimidazol-2-yl)-2,2-difluorocyclopropyl]benzenesulfonamide;
4-[(1R,3R)-3-(4,6-Difluoro-1,3-benzoxazol-2-yl)-2,2-dimethyl-cyclopropyl]benzenesulfonamide;
4-[(1R,3R)-3-(6-Fluoro-1,3-benzoxazol-2-yl)-2,2-dimethyl-cyclopropyl]benzenesulfonamide;
4-[(1R,3R)-3-(1,3-Benzothiazol-2-yl)-2,2-dimethyl-cyclopropyl]benzenesulfonamide;
4-[(1S,2S)-2-(1,3-Benzoxazol-2-yl)cyclopropyl]benzenesulfonamide;
4-[(1R,3R)-3-(6-Chloro-1,3-benzoxazol-2-yl)-2,2-dimethyl-cyclopropyl]benzenesulfonamide;
4-[(1R,3R)-3-(5-Chloro-1,3-benzoxazol-2-yl)-2,2-dimethyl-cyclopropyl]benzenesulfonamide;
4-[(1 S,2S)-2-(6-Fluoro-1,3-benzoxazol-2-yl)cyclopropyl]benzenesulfonamide;
4-[(1R,3R)-3-(4,6-Difluoro-1,3-benzothiazol-2-yl)-2,2-dimethyl-cyclopropyl]benzenesulfonamide;
4-[(1R,3R)-3-(6-Fluoro-1,3-benzothiazol-2-yl)-2,2-dimethyl-cyclopropyl]benzenesulfonamide;
4-[(1R,3R)-3-(5-Methoxy-1,3-benzoxazol-2-yl)-2,2-dimethyl-cyclopropyl]benzenesulfonamide;
4-[(1S,3S)-3-(1,3-Benzoxazol-2-yl)-2,2-difluoro-cyclopropyl]benzenesulfonamide;
4-[(1S,3R)-3-(1,3-Benzothiazol-2-yl)-2,2-difluoro-cyclopropyl]benzenesulfonamide,
4-[(1S,3S)-2,2-Dimethyl-3-quinazolin-2-yl-cyclopropyl]benzenesulfonamide;
4-[(1S,3S)-3-(5-Fluoroquinazolin-2-yl)-2,2-dimethyl-cyclopropyl]benzenesulfonamide;
4-[(1S,3S)-2,2-Dimethyl-3-(4,5,6,7-tetrahydro-1,3-benzoxazol-2-yl)cyclopropyl]benzenesulfonamide;
4-[(1R,3R)-2,2-Difluoro-3-(4,5,6,7-tetrahydro-1,3-benzoxazol-2-yl)cyclopropyl]benzenesulfonamide;
4-[(1R,3R)-2,2-Dimethyl-3-quinazolin-2-yl-cyclopropyl]benzenesulfonamide;
4-[(1R,3R)-2,2-Dimethyl-3-oxazolo[5,4-c]pyridin-2-yl-cyclopropyl]benzenesulfonamide;
4-[(1R,3R)-2,2-Dimethyl-3-(4,5,6,7-tetrahydro-1,3-benzoxazol-2-yl)cyclopropyl]benzenesulfonamide;
4-[(1R,3R)-3-(5,7-Difluoro-1-methyl-benzimidazol-2-yl)-2,2-dimethyl-cyclopropyl]benzenesulfonamide;
4-[(1S,3S)-3-(4,4-Dimethyl-4H-3,1-benzoxazin-2-yl)-2,2-difluorocyclopropyl]benzenesulfonamide;
4-[2-(2-Methyl-1,3-benzothiazol-4-yl)cyclopropyl]benzenesulfonamide;
4-[2-(7-Chloro-1,5-naphthyridin-3-yl)cyclopropyl]benzenesulfonamide;
4-(2-Pyrazolo[1,5-a]pyridin-3-ylcyclopropyl)benzenesulfonamide;
4-(2-Quinoxalin-6-ylcyclopropyl)benzenesulfonamide;
4-[2-[3-(Trifluoromethyl)cinnolin-7-yl]cyclopropyl]benzenesulfonamide;

4-[2-(3-Chloro-7-isoquinolyl)cyclopropyl]benzenesulfonamide;
4-(2-Thieno[2,3-c]pyridin-2-ylcyclopropyl)benzenesulfonamide;
4-[2-(1,7-Naphthyridin-2-yl)cyclopropyl]benzenesulfonamide;
4-[2-(1-Methylindazol-5-yl)cyclopropyl]benzenesulfonamide;
4-[2-(4,5,6,7-Tetrahydropyrazolo[1,5-a]pyridin-2-yl)cyclopropyl]benzenesulfonamide;
4-(2-Furo[2,3-b]pyridin-5-ylcyclopropyl)benzenesulfonamide;
4-[2-(2-Methylindazol-6-yl)cyclopropyl]benzenesulfonamide;
4-[2-(4-Methyl-2,3-dihydropyrido[3,2-b][1,4]oxazin-7-yl)cyclopropyl]benzenesulfonamide; and
4-[2-(5,6,7,8-Tetrahydroquinolin-3-yl)cyclopropyl]benzenesulfonamide.

Other embodiments of the present invention include the following:

(a) A pharmaceutical composition comprising a compound of formula I and a pharmaceutically acceptable carrier.

(b) The pharmaceutical composition of (a), further comprising a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(c) The pharmaceutical composition of (b), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(d) A pharmaceutical combination that is (i) a compound of formula I and (ii) a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa wherein the compound of formula I and the second therapeutic agent are each employed in an amount that renders the combination effective for treating cognitive impairments associated with Alzheimer's disease, Parkinson's disease, and schizophrenia.

(e) The combination of (d), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(f) A use of a compound of formula I in the preparation of a medicament for modulating α7 nAChR activity in a subject in need thereof.

(g) A use of a compound of formula I in the preparation of a medicament for treating cognitive impairments associated with Alzheimer's disease, Parkinson's disease, and schizophrenia in a subject in need thereof.

(h) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject an effective amount of a compound of formula I.

(i) The method of (h), wherein the compound of formula I is administered in combination with an effective amount of at least one second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(j) The method of (i), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(k) A method of modulating α7 nAChR activity in a subject in need thereof, which comprises administering to the subject the pharmaceutical composition of (a), (b), or (c) or the combination of (d) or (e).

(l) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the invention include the pharmaceutical compositions, combinations, uses and methods set forth in (a) through (l) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) preventing or treating cognitive impairments associated with Alzheimer's disease, Parkinson's disease, schizophrenia, and L-DOPA induced-dyskinesia, or (b) treating cognitive impairments associated with Alzheimer's disease, Parkinson's disease, schizophrenia, and L-DOPA induced-dyskinesia and/or reducing the likelihood or severity of symptoms of cognitive impairments associated with Alzheimer's disease, Parkinson's disease, schizophrenia, and L-DOPA induced-dyskinesia, or (c) use in medicine. In these uses, the compounds of the present invention can optionally be employed in combination with one or more second therapeutic agents selected from acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as B140936; HDAC6 inhibitors; antipsychotics; LRRK2 inhibitors; MAO-B inhibitors; and levodopa.

Chemical names, common names, and chemical structures may be used interchangeably to describe the same structure.

As used herein, the term "bicyclic heteroaryl ring" refers to a bicyclic ring system comprising 6 to 14 ring atoms, wherein from 1 to 6 of the ring atoms is independently O, N, or S and the remaining ring atoms are carbon atoms, and wherein at least one ring is aromatic. A bicyclic heteroaryl ring within the scope of this definition includes but is not limited to: benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl, dihydropyridooxazinyl, tetrahydrobenzothiazolyl, tetrahydroquinazolinyl, benzoxazinyl, benzimidazolyl, thiazolopyridinyl, quinolinyl, pyridopyrimidinyl, phthalazinyl, pyridopyrazinyl, thienoxazole, and thienothiazole.

As used herein, the term "administration" and variants thereof (e.g., "administering" a compound) in reference to a compound of the invention means providing the compound to the individual in need of treatment. When a compound of the invention is provided in combination with one or more other active agents (e.g., cholinesterase inhibitors such as donepezil, rivastigmine, and galantamine), "administration" and its variants are each understood to include concurrent and sequential provision of the compound or salt and other agents.

The term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from 1 to 12 carbon atoms. In different embodiments, an alkyl group contains from 1 to 6 carbon atoms [($C_1$-$C_6$)alkyl] or from 1 to 4 carbon atoms [($C_1$-$C_4$)alkyl] or from 1 to 3 carbon atoms [($C_1$-$C_3$)alkyl]. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "alkynyl" refers to a hydrocarbon radical straight or branched containing from 2 to 12 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. In one embodiment, an alkynyl group is linear. In another embodiment, an alkynyl group is branched.

The term "aryl" (or "aryl ring system") refers to any mono- and poly-carbocyclic ring systems wherein the individual carbocyclic rings in the polyring systems are fused or attached to each other via a single bond and wherein at least one ring is aromatic. Suitable aryl groups include phenyl, indanyl, naphthyl, tetrahydronaphthyl, and biphenyl. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "composition" is intended to encompass a product comprising the specified ingredients, as well as any product which results from combining the specified ingredients.

The term "compound" is intended to encompass chemical agents described by generic formula I in all forms. Such chemical agents can be present in different forms such as hydrates, solvates, and polymorphs.

The term "cycloalkyl" as used herein, refers to a non-aromatic mono- or multicyclic ring system comprising from 3 to 10 ring carbon atoms. In one embodiment, a cycloalkyl contains from 5 to 10 ring carbon atoms. In another embodiment, a cycloalkyl contains from 3 to 7 ring atoms. In another embodiment, a cycloalkyl contains from 3 to 6 ring atoms [($C_3$-$C_6$)cycloalkyl]. In another embodiment, a cycloalkyl contains from 5 to 7 ring atoms. In another embodiment, a cycloalkyl contains from 5 to 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0]hexyl and adamantyl. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

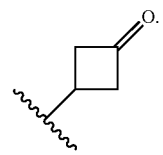 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate α7 nAChR activity and thereby elicit the response being sought (i.e., a "therapeutically effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro, chloro, bromo, and iodo).

The term "heteroaryl" as used herein, refers to any monocyclic or multicyclic ring system comprising 5 to 14 ring atoms, wherein from 1 to 4 of the ring atoms is independently O, N, or S and the remaining ring atoms are carbon atoms, and wherein at least one ring is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is usually joined via a ring carbon atom but may be joined via a non-carbon atom provided that this results in a stable compound, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O, and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzoyl and the like, and all isomeric forms thereof. The term "heteroaryl" also refers to partially saturated heteroaryl moieties such as, for example, tetrahydroisoquinolyl, tetrahydroquinolyl and the like, provided that they contain at least one aromatic ring. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

The term "heterocycle" or "heterocyclyl" as used herein is intended to mean a 3- to 10-membered non-aromatic heterocycle containing from 1 to 4 heteroatoms selected from the group consisting of O, N, and S, and includes monocyclic or bicyclic groups (fused, bridged or spirocyclic). Further examples of "heterocyclyl" include, but are not limited to the following: oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, and tetrahydrothienyl, and N-oxides thereof. Attachment of a heterocyclyl substituent can occur via a carbon atom or via a heteroatom.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms. The term "C$_1$-C$_4$ hydroxyalkyl" refers to a hydroxyalkyl group having from 1 to 4 carbon atoms. The term "C$_1$-C$_3$ hydroxyalkyl" refers to a hydroxyalkyl group having from 1 to 3 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing" as used herein with respect to Alzheimer's disease or other neurological diseases, refers to reducing the likelihood of disease progression.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In another embodiment of formula I, A is a bicyclic heteroaryl ring which is substituted with 0 to 4 R groups.

In another embodiment of formula I, A is a bicyclic heteroaryl ring which is substituted with 0 to 2 R groups.

In another embodiment of formula I, A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl, dihydropyridooxazinyl, tetrahydrobenzothiazolyl, tetrahydroquinazolinyl, benzoxazinyl, benzimidazolyl, thiazolopyridinyl, quinolinyl, pyridopyrimidinyl, phthalazinyl, pyridopyrazinyl, thienoxazole, and thienothiazole each optionally substituted with 1 to 2 R groups.

In another embodiment of formula I, A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, tetrahydroquinazolinyl, benzoxazinyl, benzimidazolyl, furopyridinyl and dihydropyridooxazinyl each optionally substituted with 1 to 2 R groups.

In another embodiment of formula I, R groups are independently selected from OH, oxo, amino, amido, carboxyl, keto, CN, alkoxy, $S(O)_m$-alkyl, halogen, aminoalkyl, hydroxyalkyl, alkyl, cycloalkyl, alkynyl, aryl, heteroaryl, and heterocyclyl, wherein said amino, amido, carboxyl, keto, alkoxy, $S(O)_m$-alkyl, aminoalkyl, hydroxyalkyl, alkyl, cycloalkyl, alkynyl, aryl, heteroaryl and heterocyclyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(O)_m$—$(C_1-C_4)$alkyl, C=O $(C_1-C_4)$alkyl, (C=O)$NR^7R^8$, (C=O)$OR^7$, $(C_2-C_4)$alkynyl, $(C_3-C_6)$cycloalkyl, $O(C_3-C_6)$cycloalkyl, C=O$(C_3-C_6)$cycloalkyl, aryl, heteroaryl and heterocyclyl, wherein said alkyl, aryl, heteroaryl and heterocyclyl are optionally independently substituted with one or more halogen, $CF_3$, OH and oxo.

In another embodiment of formula I, R groups are independently selected from OH, oxo, amino, amido, carboxyl, keto, CN, alkoxy, $S(O)_m$-alkyl, halogen, aminoalkyl, hydroxyalkyl, alkyl, cycloalkyl, alkynyl, and phenyl, wherein said amino, amido, carboxyl, keto, alkoxy, $S(O)_m$-alkyl, aminoalkyl, hydroxyalkyl, alkyl, cycloalkyl, alkynyl, and phenyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(O)_m$—$(C_1-C_4)$alkyl, C=O$(C_1-C_4)$alkyl, (C=O)$NR^7R^8$, (C=O)$OR^7$, $(C_2-C_4)$alkynyl, $(C_3-C_6)$cycloalkyl, $O(C_3-C_6)$cycloalkyl, C=O$(C_3-C_6)$cycloalkyl, aryl, heteroaryl and heterocyclyl, wherein said alkyl, aryl, heteroaryl and heterocyclyl are optionally independently substituted with one or more halogen, $CF_3$, OH and oxo.

In another embodiment of formula I, R groups are independently selected from OH, oxo, amino, amido, carboxyl, keto, CN, alkoxy, $S(O)_m$-alkyl, halogen, aminoalkyl, hydroxyalkyl, alkyl, cycloalkyl, alkynyl, and phenyl, wherein said amino, amido, carboxyl, keto, alkoxy, $S(O)_m$-alkyl, aminoalkyl, hydroxyalkyl, alkyl, cycloalkyl, alkynyl, and phenyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(O)_m$—$(C_1-C_4)$alkyl, C=O$(C_1-C_4)$alkyl, (C=O)$NR^7R^8$, (C=O)$OR^7$, $(C_2-C_4)$alkynyl, $(C_3-C_6)$cycloalkyl, $O(C_3-C_6)$cycloalkyl, C=O$(C_3-C_6)$cycloalkyl, and phenyl, wherein said alkyl and phenyl are optionally independently substituted with one or more halogen, $CF_3$, OH and oxo.

In another embodiment of formula I, R groups are independently selected from OH, oxo, amino, amido, carboxyl, keto, CN, alkoxy, $S(O)_m$-alkyl, halogen, aminoalkyl, hydroxyalkyl, and alkyl, wherein said amino, amido, carboxyl, keto, alkoxy, $S(O)_m$-alkyl, aminoalkyl, hydroxyalkyl, and alkyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(O)_m$—$(C_1-C_4)$alkyl, C=O$(C_1-C_4)$alkyl, (C=O)$NR^7R^8$, (C=O)$OR^7$, $(C_2-C_4)$alkynyl, $(C_3-C_6)$cycloalkyl, $O(C_3-C_6)$cycloalkyl, C=O$(C_3-C_6)$cycloalkyl, and phenyl, wherein said alkyl and phenyl are optionally independently substituted with one or more halogen, $CF_3$, OH and oxo.

In another embodiment of formula I, R groups are independently selected from halogen, $(C_1-C_4)$alkyl, $O(C_1-C_4)$alkyl and $CF_3$.

In another embodiment of formula I, X is selected from

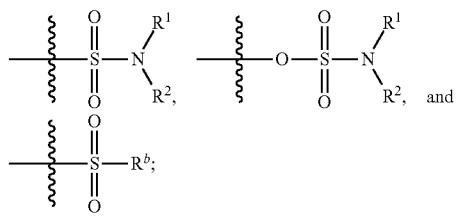

wherein $R^1$, $R^2$, and $R^b$ is H.

In another embodiment of formula I, X is

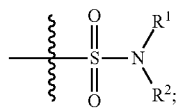

wherein $R^1$ and $R^2$ are H.

In another embodiment of formula I, Y is 4 substituents, each independently selected from H, $(C_1-C_4)$alkyl, halogen, and OH, wherein said alkyl is optionally substituted with one or more halogen or OH.

In another embodiment of formula I, Y is H.
In another embodiment of formula I, $R^1$ is H or methyl.
In another embodiment of formula I, $R^2$ is H or methyl.
In another embodiment of formula I or Ia, $R^3$ is H, F or methyl.
In another embodiment of formula I or Ia, $R^4$ is H, F or methyl.
In another embodiment of formula I, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl.
In another embodiment of formula I, $R^3$ and $R^4$ optionally can come to together to form a cyclopropyl, cyclobutyl, cyclopentyl or cyclohexyl ring.
In another embodiment of formula I, $R^5$ is H or methyl.
In another embodiment of formula I, $R^6$ is H or methyl.
In another embodiment of formula I, $R^7$ is H or methyl.
In another embodiment of formula I, $R^8$ is H or methyl.
In another embodiment of formula I, $R^a$ is H or methyl.
In another embodiment of formula I, $R^b$ is H or methyl.
In another embodiment of formula I, $R^5$ is H.
In another embodiment of formula I, $R^6$ is H.
In another embodiment of formula I, $R^a$ is H.
In another embodiment of formula I, $R^b$ is H.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

It is understood by one skilled in the art that carbon atoms in organic molecules may often be replaced by silicon atoms to give analogous stable compounds. For example, carbon atoms in alkoxy, alkyl, cycloalkyl, heteroaryl, heterocyclyl, and hydroxyalkyl groups may often be replaced by silicon atoms to provide stable compounds. All such compounds are within the scope of the present invention.

When any variable (for example, R) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present invention may have utility in preventing, treating, or ameliorating Alzheimer's disease. The compounds may also be useful in preventing, treating, or ameliorating other diseases mediated by the α7 nAChR, such as schizophrenia, sleep disorders, Parkinson's disease, autism, microdeletion syndrome, inflammatory diseases, pain disorders (including acute pain, inflammatory pain and neuropathic pain) and cognitive disorders (including mild cognitive impairment). Other conditions that may be prevented, treated, or ameliorated by the compounds of the invention include pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, kidney diseases, cancer, and atherosclerosis.

In preferred embodiments, the compounds of the invention may be useful in preventing, treating, or ameliorating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

Thus, in another specific embodiment, the present invention provides a method for preventing, treating, or ameliorating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression; emotional/mood disorders; as well as sleep walking and enuresis; and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis); repetitive motion pain; dental pain; cancer pain; myofascial pain (muscular injury, fibromyalgia); perioperative pain (general surgery, gynecological); chronic pain; dysmennorhea, as well as pain associated with angina, and inflammatory pain of varied origins (e.g. osteoarthritis, rheumatoid arthritis, rheumatic disease, teno-synovitis and gout); headache; migraine and cluster headache; primary hyperalgesia; secondary hyperalgesia; primary allodynia; secondary allodynia; or other pain caused by central sensitization.

Potential conditions or disorders that have a strong inflammatory component for which the compounds of the invention may be useful include one or more of the following conditions or diseases: diabetes (systemic inflammation in diabetes marked by increases in blood cytokines e.g. IL-6 and TNFα which may lead to insulin resistance); asthma; arthritis; cystic fibrosis; sepsis; ulcerative colitis; inflammatory bowel disease; atherosclerosis; neuroinflammation associated with neurodegenerative diseases (e.g. Alzheimer's disease, Parkinson's disease, Creutzfeldt-Jacob disease, frontotemporal dementia, corticobasal degeneration, Pick's disease, progressive supranuclear palsy, traumatic brain injury, Huntington's disease, amyotrophic lateral sclerosis).

Compounds of the invention may also be used to treat or prevent or ameliorate dyskinesia and protect against neurodegeneration in nigrostriatal neurons in Parkinson's disease. Furthermore, compounds of the invention may be used to decrease tolerance and/or dependence to opioid treatment of pain, and for treatment of withdrawal syndrome of e.g., alcohol, opioids, and cocaine.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1):1-19; P. Gould, *International J of Pharmaceutics* (1986) 33:201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of preventing, treating, or ameliorating the cognitive impairments in Alzheimer's disease, Parkinson's disease, schizophrenia, L-DOPA induced-dyskinesia, and inflammation, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrastemal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition.

As noted above, the present invention also relates to a method of preventing, treating, or ameliorating the cognitive impairments in Alzheimer's disease, Parkinson's disease, schizophrenia, L-DOPA induced-dyskinesia, and inflammation with a compound of the present invention in combination with one or more therapeutic agents and a pharmaceutical composition comprising a compound of the present invention and one or more therapeutic agents selected from the group consisting of anti-Alzheimer's Disease agents, for example beta-secretase inhibitors such as verubecestat; M1 mAChR agonist or PAMs; M4 mAChR agonists or PAMs; mGluR2 antagonists or NAMs or PAMs; ADAM 10 ligands or activators; gamma-secretase inhibitors, such as LY450139 and TAK 070; gamma secretase modulators; tau phosphorylation inhibitors; glycine transport inhibitors; LXR 3 agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; LRRK2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; GABAA inverse agonists; GSK30 inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds of the instant invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the compounds of the instant invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride; COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compound of the instant invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the compounds of the instant invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compounds of the instant invention may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds of the instant invention include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED 160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGN XX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, rameltoen, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

Compounds of the instant invention are useful for the treatment of moderate to severe dementia of the Alzheimer's type alone or in combination with an NMDA receptor antagonist, such as memantine, or in combination with an acetylcholinesterase inhibitor (AChEI) such as donepezil.

Compounds of the instant invention are useful for the treatment of mild to moderate dementia of the Alzheimer's type alone or in combination with either galantamine, rivastigmine, or donepezil.

Compounds of the instant invention are useful for the treatment of dementia associated with Parkinson's disease alone or in combination with rivastigmine.

Compounds of the instant invention are useful for the treatment of motor fluctuations in patients with advanced Parkinson's disease alone or in combination with carbidopa and levodopa.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The α7 nAChR positive allosteric modulator (PAM) activity of the present compounds may be tested using assays known in the art. The α7 nAChR PAMs described herein have activities in an automated patch-clamp electrophysiology functional assay as described in the examples. The assay was performed using the IonFlux HT in a whole-cell, population patch configuration. See Golden et al. *Assay Drug Dev. Technol.* (2011) 9:608-619. The compounds were assessed for their ability to modulate the function of the human 07 nAChR stably expressed in a HEK cell line both in the presence, and in the absence of the natural 07 agonist acetylcholine. By performing a series of such measurements at different concentrations, the effective concentration of the α7 nAChR PAMs ($EC_{50}$) was determined. See Spencer et al. *Assay Drug Dev. Technol.* (2012) 10:313-324.

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Reaction Schemes

The compounds of the present invention can be prepared readily according to the following Schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Many compounds of the present invention may be prepared according to Scheme 1, in which acid 1.1 is first reacted with oxalyl chloride in the presence of catalytic DMF and the resulting acid chloride treated with aminophenol 1.2 in dioxane to afford the corresponding amide. The resultant amide is then treated with TsOH at elevated temperature to give product 1.3. Other coupling conditions, including reagents such as EDC and HOAt, and dehydrating reagents, such as phosphorous oxychloride, can be employed in these transformations. If 1.3 is a mixture of enantiomers or diastereomers, the mixture may be separated by chiral chromatography. Alternatively, 1.1 and 1.2 may be employed as single enantiomers or diastereomers to obtain 1.3 enriched in a single enantiomer or diastereomer. Other methods of forming the benzoxazole may also be employed, such as treating a solution of 1.1 and 1.2 with trimethylsilyl polyphosphate at elevated temperature. Additionally, the benzothiazole variant of 1.3 may be obtained by employing an aminothiophenol in place of aminophenol 1.2.

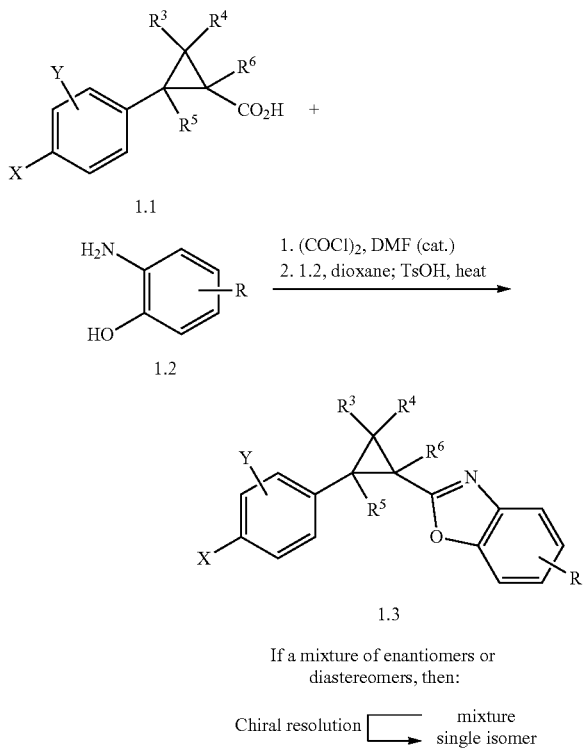

Additional compounds of the present invention may be prepared according to Scheme 2, in which acid 1.1 is reacted with aniline 2.1 in the presence of HATU and NMM, then the resulting amide treated with acetic acid at elevated temperature to effect dehydrative heterocycle formation, and, finally, the resultant dihydroquinazoline treated with Dess-Martin periodinane to afford product 2.2. Other coupling, dehydrating, and oxidizing reagents and conditions can be employed to effect these transformations.

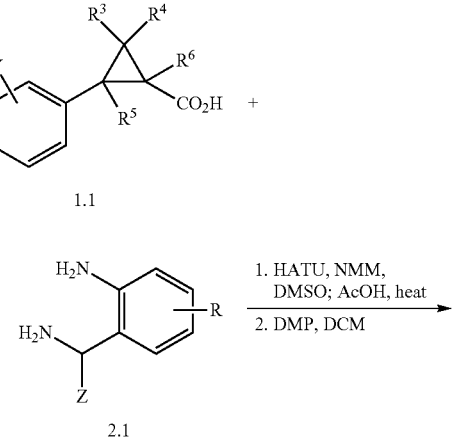

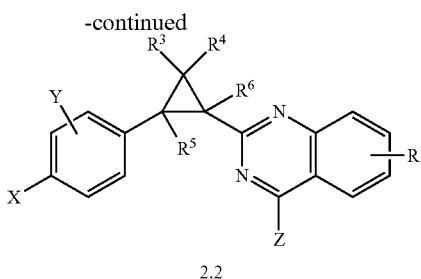

2.2

Further compounds of the present invention may be prepared according to Scheme 3, in which acid 1.1 is reacted with amino ketone 3.1 in the presence of HATU and NMM and the resulting amide treated with phosphorous oxychloride at elevated temperature to effect cyclodehydration and afford oxazole bicycle 3.2. Other coupling and dehydrating reagents and conditions can be employed to effect these transformations. Additionally, the corresponding amino alcohol of 3.1 could be employed in a similar sequence with the addition of an oxidizing reagent, if necessary, to furnish 3.2.

SCHEME 3

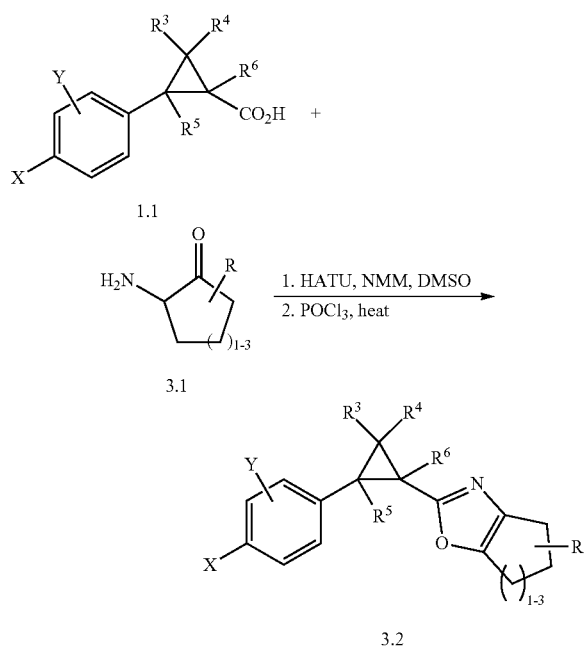

Other compounds of the present invention may be prepared according to Scheme 4, in which acid 4.1 is first treated with Ghosez's reagent in the presence of triethylamine and the resulting acid chloride reacted with aminophenol 4.2 in dichloromethane at elevated temperature to afford the corresponding amide. The resultant amide is then treated with hexachloroethane, triphenylphosphine, and triethylamine at elevated temperature to effect cyclodehydration and the resultant protected bicyclic product treated with TFA in DCM to afford product 4.3. Other coupling conditions, including reagents such as EDC and HOAt, and other phosphines, such as tributylphosphine, halogen sources, such as $CCl_4$ or $I_2$, and bases can be employed in these transformations.

SCHEME 4

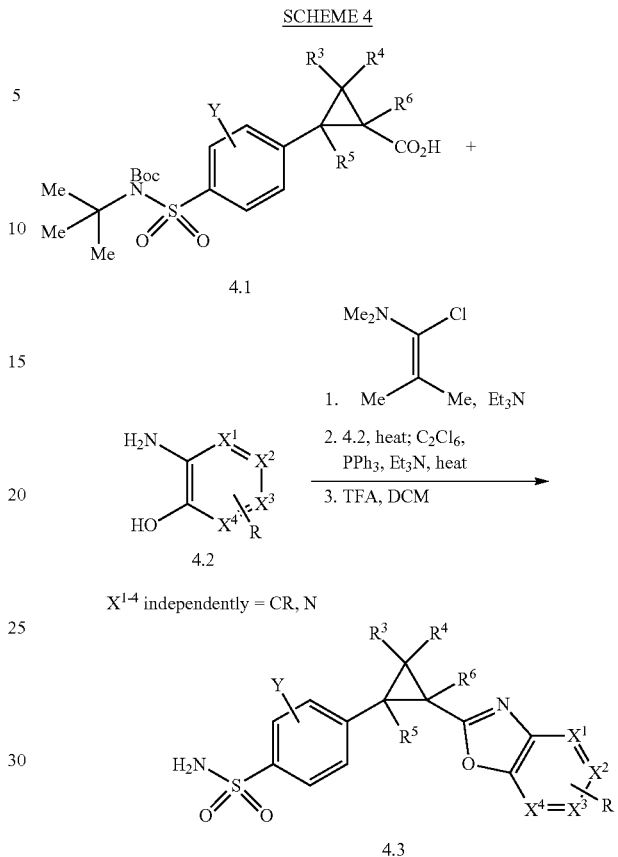

$X^{1-4}$ independently = CR, N

Additional compounds of the present invention may be prepared according to Scheme 5, in which boronic acid 5.1 is reacted with bicyclic bromide 5.2, which may be aryl or heteroaryl, under palladium-catalyzed conditions followed by treatment with hydrazine hydrate to afford product 5.3. Similar chemistry may be performed using a boronate ester or boronic acid derivative in place of the boronic acid and a chloride, iodide, triflate, or tosylate, for example, as alternatives to bromide. A variety of different catalysts, which includes other metals such as nickel, ligands, bases, and solvents can be employed in this reaction.

SCHEME 5

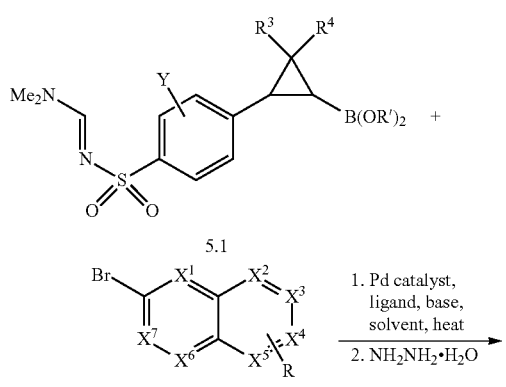

$X^{1-7}$ independently = CR, N

-continued

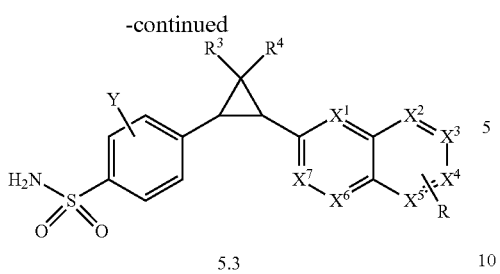

5.3

Other compounds of the present invention may be prepared according to Scheme 6, in which pinacol boronate 6.1 is reacted with 2-bromoquinoxaline (6.2) under palladium-catalyzed conditions followed by treatment with hydrazine hydrate to afford product 6.3. A variety of different catalysts, which includes other metals such as nickel, ligands, bases, and solvents can be employed in this reaction.

SCHEME 6

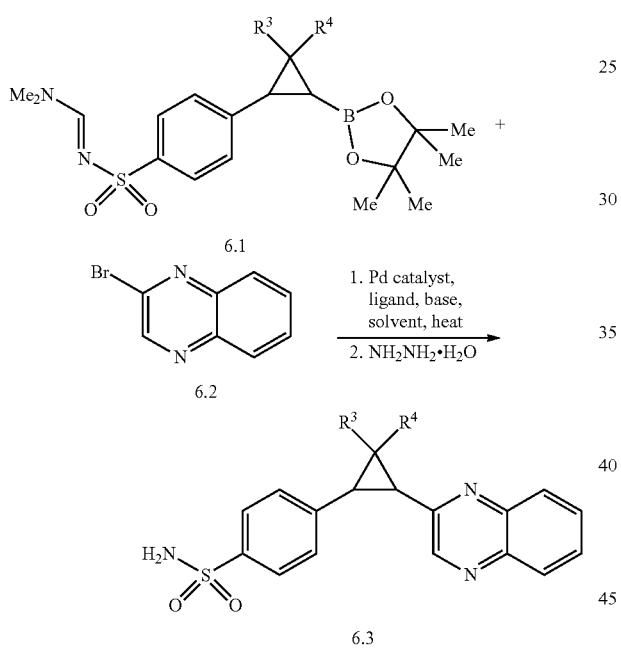

Further compounds in the present invention may be prepared according to Scheme 7, in which haloketone 7.1 is reacted with aminopyridazine 7.2 in the presence of sodium bicarbonate in ethanol at elevated temperature to afford product 7.3. Other bases, halides, and solvents can be employed to effect this transformation as well.

SCHEME 7

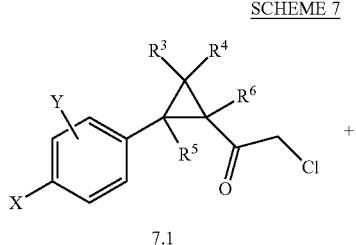

7.1

-continued

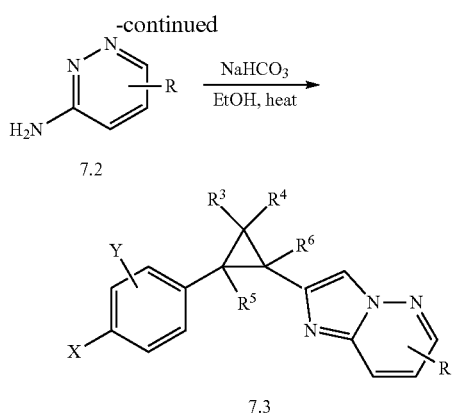

Additional compounds of the present invention may be prepared according to Scheme 8, in which acid 1.1 is first reacted with aniline 8.1 in the presence of HATU and Hunig's base to give the corresponding amide. The resultant amide is then treated with copper iodide and sodium sulfide at elevated temperature to install a thiophenol moiety and then treated with HCl to effect dehydrative heterocycle formation, affording product 8.2. Other coupling reagents, copper salts, and sulfur sources can be employed to effect these transformations.

SCHEME 8

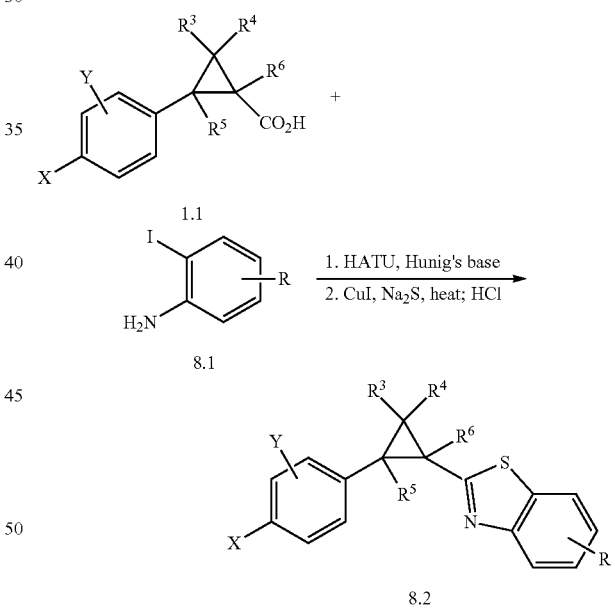

Useful synthetic intermediates like 9.3 may be prepared according to Scheme 9. The sequence begins with sulfonylation of ester 9.1 by treatment with neat chlorosulfonic acid followed by treatment of the resultant sulfonyl chloride with a solution of ammonia in a solvent, such as water, 1,4-dioxane, tetrahydrofuran, and methanol, and chiral resolution of the isomeric mixture to afford enantiopure sulfonamide 9.2. Similar chemistry may be carried out employing a mixture of a halogenated solvent and chlorosulfonic acid as opposed to the neat acid. Ester 9.2 can then be saponified by treatment with sodium hydroxide to afford acid 9.3. Other bases, such as lithium hydroxide or potassium trimethylsilanolate, can be employed in this transformation.

SCHEME 9

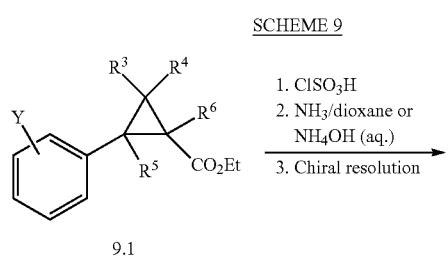
9.1

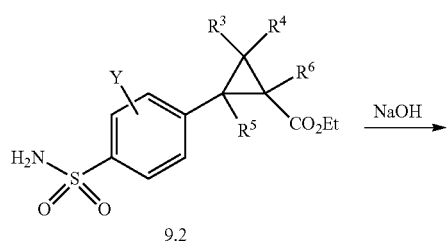
9.2

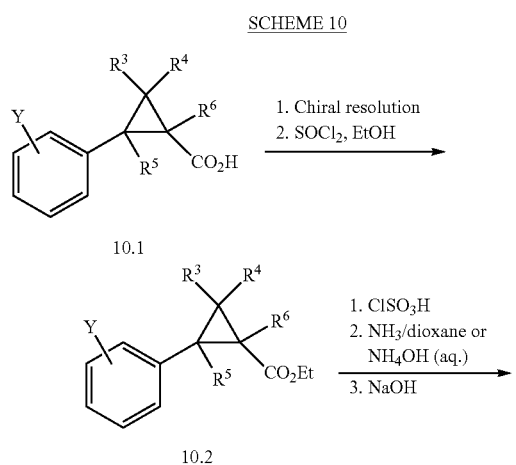
9.3

Another approach to intermediates like 9.3 is illustrated in Scheme 10. The sequence begins with chiral resolution of an isomeric mixture of acid 10.1 followed by esterification of the resulting enantiopure acid by treatment with thionyl chloride in ethanol to afford ester 10.2. Next, ester 10.2 is sulfonylated by treatment with neat chlorosulfonic acid (or a mixture of a halogenated solvent and chlorosulfonic acid) followed by treatment of the resultant sulfonyl chloride with a solution of ammonia in a solvent (e.g. water, dioxane, tetrahydrofuran, methanol). Saponification of the resulting sulfonamide then affords acid 9.3. Other methods of esterification, such as by use of an alkyl halide and a base, and other bases for the saponification can be employed in this sequence.

SCHEME 10

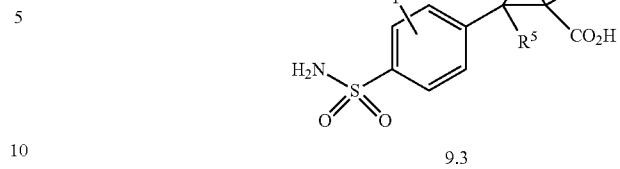
9.3

Intermediates like 4.1 may be prepared according to Scheme 11. Sulfonamide 9.2 is treated with di-tert-butyl dicarbonate in the presence of DMAP at elevated temperature followed by saponification of the resulting bis-protected sulfonamide to afford acid 4.1. Other standard saponification conditions can be employed in this sequence.

SCHEME 11

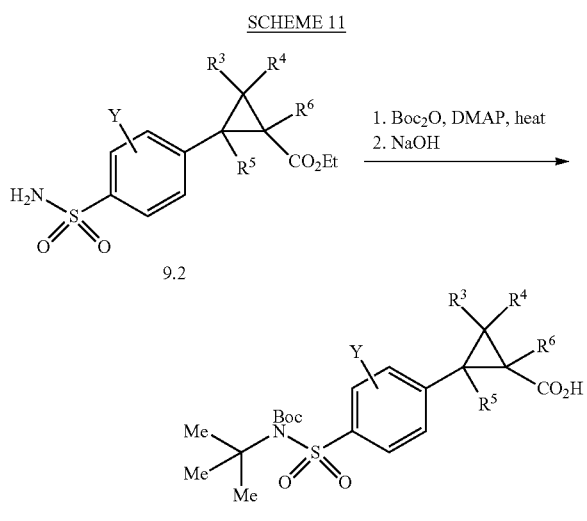
4.1

Other useful intermediates like 6.1 may be prepared according to Scheme 12. The sequence begins with treating sulfonamide 12.1 with DMF-DMA at elevated temperature to afford aryl bromide 12.2. Aryl bromide 12.2 is then reacted with alkenyl boronate 12.3 under palladium-catalyzed conditions to afford styrenyl boronate 12.4. A variety of different catalysts, which includes other metals such as nickel, ligands, bases, and solvents can be employed in this reaction. Styrenyl boronate 12.4 can then be treated with TMSD in the presence of palladium acetate followed by treatment of the resulting cyclopropane with triflic acid to afford cyclopropyl boronate 12.5. Other palladium, copper, and rhodium catalysts can be employed in the cyclopropanation reaction.

SCHEME 12

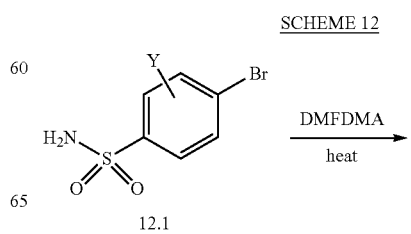
12.1

-continued

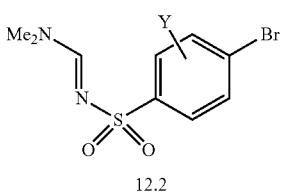

12.2

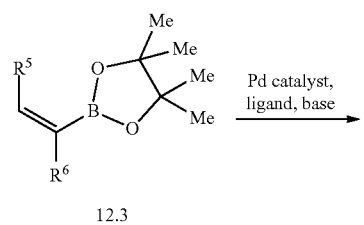

12.3

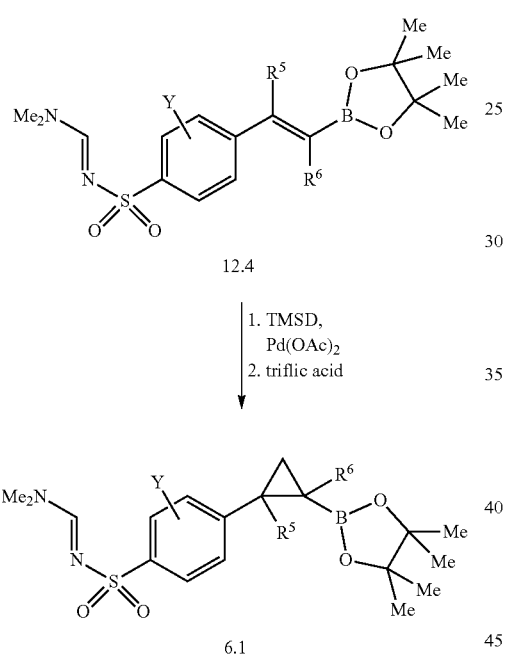

12.4

1. TMSD, Pd(OAc)$_2$
2. triflic acid 6.1

Haloketone intermediates of interest like 7.1 may be prepared according to Scheme 13, in which acid 1.1 is treated with sulfuric acid in the presence of methanol and then reacting the resultant ester with chloroiodomethane in the presence of LDA to afford haloketone 7.1. Other bases can be employed in this transformation.

SCHEME 13

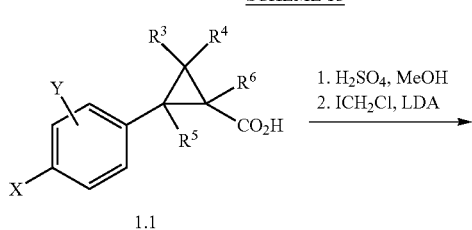

1.1

-continued

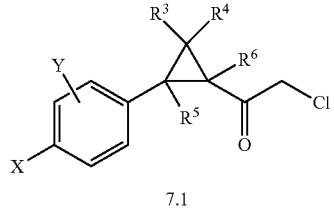

7.1

Scheme 14 illustrated the synthesis of a tetrahydroquinazoline-based compound of the present invention. The amidine 14.1 may be readily accessed from intermediates like carboxylic acid 1.1 using standard methodology that is well known to one skilled in the art. Reaction of such an amidine with ketone 14.2 under basic conditions, for example using sodium methoxide or sodium ethoxide in refluxing ethanol, affords the desired tetrahydroquinazoline 14.3. A variety of bicyclic systems containing a pyrimidine ring may be accessed using similar methodology.

SCHEME 14

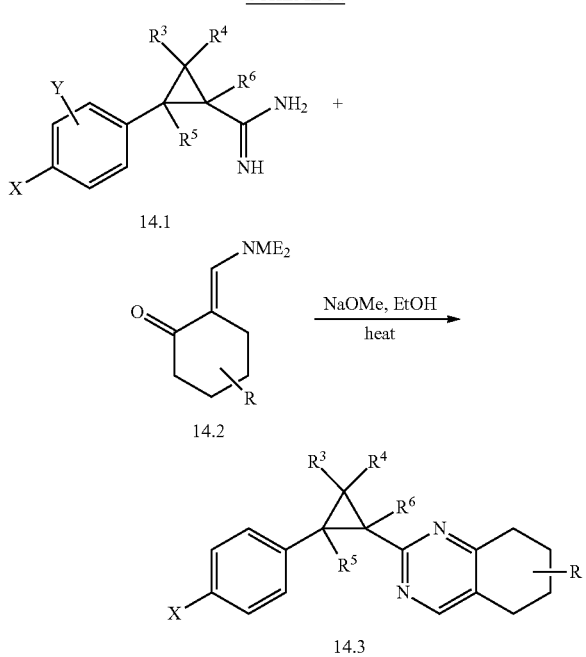

It is understood that the compounds and intermediates in the foregoing reaction schemes may be employed as synthetic intermediates in other schemes that involve similar intermediates to produce alternative compounds of the present invention.

In some cases the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

| | |
|---|---|
| Ac | Acetyl |
| AIBN | 2,2'-azobisisobutyronitrile |
| app | Apparent |
| aq | Aqueous |
| Ar | Aryl |
| $B_2(Pin)_2$ | bis(pinacolato)diboron |
| BINAP | 2,2'-bis(diphenylphosphino)-1,1'-binaphthalene |
| Bn | Benzyl |
| Boc | tert-butoxycarbonyl |
| BOP | (benzotriazol-1-yloxy)tris(dimethylamino)phosphonium hexafluorophosphate |
| br | Broad |
| BSA | bovine serum albumin |
| Bu | Butyl |
| ca | circa (approximately) |
| CAN | ammonium cerium(IV) nitrate |
| Cbz | Carboxybenzyl |
| CDI | 1,1'-carbonyldiimidazole |
| d | Doublet |
| DABCO | diazabicyclo[2.2.2]octane |
| DAST | (diethylamino)sulfur trifluoride |
| dba | Dibenzylideneacetone |
| DBU | 1,8-diazabicyclo[5.4.0]undec-7-ene |
| DCE | 1,2-dichloroethane |
| DCDMH | 1,3-dichloro-5,5-dimethylhydantoin |
| dd | doublet of doublets |
| DIBAL | diisobutylaluminum hydride |
| DIEA | N,N-diisopropylethylamine |
| DMA | N,N-dimethylacetamide |
| DMAP | 4-(dimethylamino)pyridine |
| DMEM | Dulbecco's modified eagle medium (high glucose) |
| DMF | N,N-dimethylformamide |
| DMF-DMA | N,N-dimethylformamide dimethylacetal |
| DMPU | N,N'-dimethylpropyleneurea |
| DMSO | Dimethylsulfoxide |
| DPBF | 1,3-diphenylisobenzofuran |
| dppf | 1,1'-bis(diphenylphosphino)ferrocene |
| EDC | N-(3-dimethylaminopropyl)-N'-ethylcarbodiimide hydrochloride |
| EDTA | ethylenediaminetetraacetic acid |
| EGTA | ethylene glycol-bis(β-aminoethyl ether)-N,N,N',N'-tetraacetic acid |
| eq | Equivalents |
| ESI | electrospray ionization |
| Et | Ethyl |
| FBS | fetal bovine serum |
| h | Hours |
| HATU | O-(7-azabenzotriazol-1-yl)-N,N,N'N'-tetramethyluronium hexafluorophosphate |
| HEK | human embryonic kidney |
| HEPES | N-(2-hydroxyethyl)piperazine-N'-(2-ethanesulfonic acid) |
| HMDS | Hexamethyldisilazane |
| HMTA | Hexamethylenetetramine |
| HOAt | 1-hydroxy-7-azabenzotriazole |
| HOBt | 1-hydroxybenzotriazole |
| HPLC | high performance liquid chromatography |
| Hz | Hertz |
| imid | Imidazole |
| i-Pr | Isopropyl |
| J | coupling constant |
| LAH | lithium aluminum hydride |
| LCMS | liquid chromatography-mass spectrometry |
| LDA | lithium diisopropylamide |
| m/z | mass to charge ratio |
| m | Multiplet |
| mCPBA | 3-chloroperoxybenzoic acid |
| Me | Methyl |
| min | Minutes |
| MP | macroporous polystyrene |
| Ms | Methanesulfonyl |
| MTBE | methyl tert-butyl ether |
| MW | molecular weight |
| NBS | N-bromosuccinimide |
| NHS | N-hydroxysuccinimide |
| n-BuLi | n-butyllithium |
| n-HexLi | n-hexyllithium |
| NMM | N-methyl morpholine |
| NMP | 1-methyl-2-pyrrolidinone |
| NMR | nuclear magnetic resonance |
| OAc | Acetate |
| p | Pentet |
| PBPB | pyridinium bromide perbromide |
| PBS | phosphate-buffered saline |
| PCC | pyridinium chlorochromate |
| PDC | pyridinium dichromate |
| Pd/C | palladium on carbon |
| Ph | Phenyl |
| PMBCl | 4-methoxybenzyl chloride |
| psi | pounds per square inch |
| p-Ts | para-toluenesulfonyl |
| PTSA | para-toluensulfonic acid |
| Py | Pyridyl |
| q | Quartet |
| RIC-3 | resistance to inhibitors of cholinesterase 3 |
| rt | room temperature |
| s | Singlet |
| SEM | 2-trimethylsilylethoxymethyl |
| SEMCl | 2-trimethylsilylethoxymethyl chloride |
| SFC | supercritical fluid chromatography |
| SM | starting material |
| SPE | solid phase extraction |
| t | Triplet |
| T3P | 2,4,6-tripropyl-1,3,5,2,4,6-trioxatriphosphorinane-2,4,6-trioxide |
| TBAF | n-tetrabutylammonium fluoride |
| TBDPS | tert-butyldiphenylsilyl |
| TBDPSCl | tert-butyldiphenylsilyl chloride |
| t-Bu | tert-butyl |
| TCCA | trichloroisocyanuric acid |
| TEA | Trimethylamine |
| TFA | trifluoroacetic acid |
| Tf | Trifluoromethanesulfonyl |
| TCFH | tetramethylchloroformamidinium hexafluorophosphate |
| THF | Tetrahydrofuran |
| TMG | Tetramethylguanidine |
| TMSD | Trimethylsilyldiazomethane |
| Trisyl | 2,4,6-triisopropylbenzenesulfonyl |
| V/V | volume to volume |
| X-Phos | 2-dicyclohexylphosphino-2',4',6'-triisopropylbiphenyl |
| Xantphos | (9,9-dimethyl-9H-xanthene-4,5-diyl)bis(diphenylphosphane) |

Intermediate 1

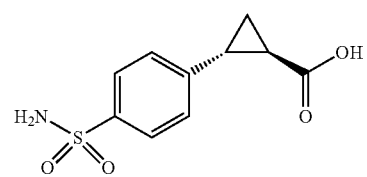 [SMILES: NS(=O)(=O)c1ccc([C@@H]2C[C@H]2C(=O)O)cc1]

(1R,2R)-2-(4-Sulfamoylphenyl)cyclopropanecarboxylic Acid

Step A: Ethyl (1R,2R)-2-(4-sulfamoylphenyl)cyclopropanecarboxylate

To a stirred solution of ethyl trans-2-phenylcyclopropanecarboxylate (700 g, 3.68 mol) in chloroform (6 L) at 0° C. was added chlorosulfonic acid (2.45 L, 36.8 mol) dropwise. The resulting mixture was allowed to warm to ambient temperature and stirring was continued for 2 h, then the reaction mixture was cooled to 0° C. and quenched by addition of water (3 L). The resulting mixture was extracted with dichloromethane (2×3 L) and the combined organic extracts were dried (sodium sulfate), filtered, and concentrated under reduced pressure. The residue was dissolved in 1,4-dioxane (15 L) and ammonium hydroxide solution (30%, 2.1 L, 18.0 mol) was added dropwise. The resulting mixture was allowed to stir for 30 min at ambient temperature and then diluted with water (10 L). The resulting mixture was extracted with ethyl acetate (3×5 L) and the combined organic extracts were washed with saturated aqueous sodium chloride (10 L), dried (sodium sulfate), filtered, and concentrated under reduced pressure to provide the racemic title compound. The enantiomers were resolved by SFC, utilizing a Chiralcel OD-H column and eluting with ethanol:carbon dioxide:diethylamine—20:80:0.2. The first major peak to elute was ethyl (1S,2S)-2-(4-sulfamoylphenyl)cyclopropanecarboxylate, and the second major peak to elute was ethyl (1R,2R)-2-(4-sulfamoylphenyl)cyclopropanecarboxylate, the title compound. MS: m/z=270.1 [M+H].

Step B: (1R,2R)-2-(4-Sulfamoylphenyl)cyclopropanecarboxylic Acid

To a stirred solution of ethyl (1R,2R)-2-(4-sulfamoylphenyl)cyclopropanecarboxylate (190 g, 0.705 mol) in tetrahydrofuran (3 L) and methanol (600 mL) at ambient temperature was added at 0° C. was added aqueous sodium hydroxide (2.12 M, 1.00 L, 2.12 mol) dropwise. The resulting mixture was allowed to stir at ambient temperature for 2 h and then concentrated under reduced pressure to remove the organic solvents. The resulting mixture was adjusted to pH=4 by addition of aqueous hydrochloric acid (2.0 M) and extracted with ethyl acetate (2×2 L) and the combined organic extracts were washed with saturated aqueous sodium chloride (1 L), dried (sodium sulfate), filtered, and concentrated under reduced pressure. The residue was purified by recrystallization from diethyl ether to afford the title compound. MS: m/z=242.1 [M+H].

Intermediate 2

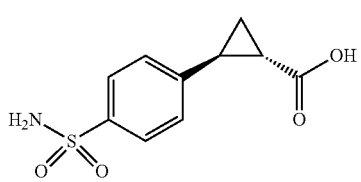 [SMILES: NS(=O)(=O)c1ccc([C@H]2C[C@@H]2C(=O)O)cc1]

(1S,2S)-2-(4-Sulfamoylphenyl)cyclopropanecarboxylic Acid

Essentially following the procedures described in Intermediate 1, but using ethyl (1S,2S)-2-(4-sulfamoylphenyl) cyclopropanecarboxylate (described in Intermediate 1) in place of ethyl (1R,2R)-2-(4-sulfamoylphenyl)cyclopropanecarboxylate, the title compound was obtained. MS: m/z=242.1 [M+H].

Intermediate 3

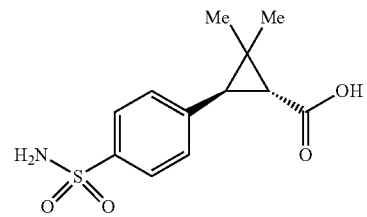 [SMILES: CC1(C)[C@H](C(=O)O)[C@H]1c1ccc(S(N)(=O)=O)cc1]

(1R,3R)-2,2-Dimethyl-3-(4-sulfamoylphenyl)cyclopropanecarboxylic Acid

Step A: (1R,3R)-2,2-Dimethyl-3-phenylcyclopropanecarboxylic Acid

The enantiomers of trans-2,2-dimethyl-3-phenylcyclopropanecarboxylic acid (957 g, 5.03 mol) were resolved by SFC, utilizing a Lux-5u column and eluting with methanol: carbon dioxide—30:70. The first major peak to elute was (1R,3R)-2,2-dimethyl-3-phenylcyclopropanecarboxylic acid, the title compound, and the second major peak to elute was (1S,3S)-2,2-dimethyl-3-phenylcyclopropanecarboxylic acid. MS: m/z=191.1 [M+H].

Step B: Ethyl (1R,3R)-2,2-dimethyl-3-phenylcyclopropanecarboxylate

To a stirred solution of (1R,3R)-2,2-dimethyl-3-phenyl-cyclopropanecarboxylic acid (267 g, 1.40 mol) in ethanol (2.7 L) was added thionyl chloride (497 g, 4.21 mol) dropwise at 0° C. The resulting solution was allowed to stir for 1 h at ambient temperature and concentrated under reduced pressure. The residue was dissolved in ethyl acetate (2 L), washed with saturated aqueous sodium bicarbonate (2×1.5 L) and saturated aqueous sodium chloride (3 L), dried (magnesium sulfate), and concentrated under reduced pressure to afford the title compound. MS: m/z=219.1 [M+H].

Step C: Ethyl (1R,3R)-2,2-dimethyl-3-(4-sulfamoylphenyl)cyclopropanecarboxylate

To a stirred solution of ethyl (1R,3R)-2,2-dimethyl-3-phenylcyclopropanecarboxylate (245 g, 1.12 mol) in chloroform (2.5 L) at 0° C. was added chlorosulfonic acid (1564 g, 13.48 mol) dropwise. The resulting solution was allowed to stir for 30 min at 0° C., warmed to ambient temperature, and allowed to stir for 2 h. The reaction mixture was cooled to 0° C., water (2 L) was added, and the resulting solution was extracted with ethyl acetate (2×3 L). The organic extracts were combined, washed with saturated aqueous sodium chloride (3 L), dried (magnesium sulfate), and concentrated under reduced pressure. The residue was dissolved in 1,4-dioxane (9 L), cooled to 5° C., and ammonium hydroxide solution (30%, 1.75 L, 13.5 mol) was added. The resulting solution was allowed to stir for 30 min at ambient temperature, diluted with water (5 L), and the resulting solution extracted with ethyl acetate (3×3 L). The combined organic extracts were washed with saturated aqueous sodium chloride (5 L), dried (magnesium sulfate), and concentrated under reduced pressure. The residue was purified by silica gel chromatography, eluting with a gradient of ethyl acetate:petroleum ether—17:83 to 33:67 to afford the title compound. MS: m/z=298.0 [M+H].

Step D: (1R,3R)-2,2-Dimethyl-3-(4-sulfamoylphenyl)cyclopropanecarboxylic Acid

To a solution of (1R,3R)-ethyl 2,2-dimethyl-3-(4-sulfamoylphenyl)cyclopropanecarboxylate (15 g, 50.4 mmol) in tetrahydrofuran (400 mL) and methanol (100 mL) at ambient temperature was added sodium hydroxide (1.0 M, 150 mL, 150 mmol). The reaction mixture was warmed to 60° C. and allowed to stir for 2.5 h. The reaction mixture was cooled to 0° C., hydrochloric acid (1.00 M, 12.5 mL, 151 mmol) slowly added, and the resulting mixture concentrated under reduced pressure to remove methanol, tetrahydrofuran, and a small amount of the water. The mixture was extracted with ethyl acetate (3×200 mL) and the combined organic extracts were washed with saturated aqueous sodium chloride (150 mL), dried (sodium sulfate), filtered, and concentrated under reduced pressure to afford the title compound. MS: m/z=270.1 [M+H].

Intermediate 4

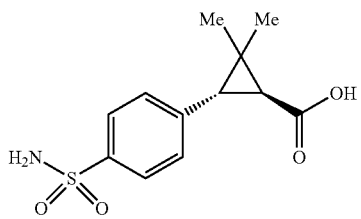 [SMILES: CC1(C)[C@@H](C(=O)O)[C@@H]1c1ccc(S(N)(=O)=O)cc1]

(1S,3S)-2,2-Dimethyl-3-(4-sulfamoylphenyl)cyclopropanecarboxylic Acid

Essentially following the procedures described in Intermediate 3, but using (1S,3S)-2,2-dimethyl-3-phenylcyclopropanecarboxylic acid (described in Intermediate 3) in place of (1R,3R)-2,2-dimethyl-3-phenylcyclopropanecarboxylic acid, the title compound was obtained. MS: m/z=270.2 [M+H].

Intermediate 5

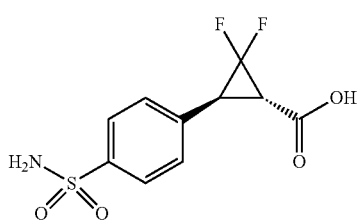 [SMILES: NS(=O)(=O)c1ccc([C@@H]2[C@@H](C(=O)O)C2(F)F)cc1]

(1S,3S)-2,2-Difluoro-3-(4-sulfamoylphenyl)cyclopropanecarboxylic Acid

Step A: Ethyl (1S,3S)-2,2-difluoro-3-(4-sulfamoylphenyl)cyclopropanecarboxylate

To chlorosulfonic acid (35.5 mL, 530 mmol) at 0° C. was added ethyl trans-2,2-difluoro-3-phenylcyclopropanecarboxylate (10.0 g, 44.2 mmol) (Dolbier et al. *J. Fluorine Chem*. (2004) 125:459-469) dropwise. The reaction mixture was allowed to stir at 0° C. for 30 min, warmed to ambient temperature, and allowed to stir for 2 h. The reaction mixture was slowly added to slowly stirred ice/water (500 mL) over the course of 5 min. The resulting suspension was then diluted with ethyl acetate (400 mL) and allowed to stir for 5 min. The layers were separated and the aqueous layer extracted with ethyl acetate (2×400 mL). The combined organic extracts were washed with water (400 mL), dried (magnesium sulfate), and concentrated under reduced pressure. The residue was dissolved in 1,4-dioxane (400 mL) and ammonium hydroxide (30%, 92 mL, 1.36 mol) was added. The reaction mixture was allowed to stir at ambient temperature for 2.5 h and then concentrated under reduced pressure. The residue was purified by silica gel chromatography, eluting with a gradient of ethyl acetate:hexanes—0:100 to 40:60 to afford the racemic title compound. The racemate was resolved by SFC, utilizing a ChiralPak AD-H column, eluting with isopropanol:carbon dioxide:diethylamine—20:80:0.1. The first major peak to elute was ethyl (1R,3R)-2,2-difluoro-3-(4-sulfamoylphenyl)cyclopropanecarboxylate and the second major peak to elute was ethyl (1S,3S)-2,2-difluoro-3-(4-sulfamoylphenyl)cyclopropanecarboxylate, the title compound. MS: m/z=306.2 [M+H].

Step B: (1S,3S)-2,2-Difluoro-3-(4-sulfamoylphenyl)cyclopropanecarboxylic Acid

To a solution of ethyl (1S,3S)-2,2-difluoro-3-(4-sulfamoylphenyl)cyclopropane carboxylate, (500 mg, 1.64 mmol) in acetonitrile (8.2 mL) was added aqueous lithium hydroxide (1.0 M, 4.9 mL, 4.9 mmol) and the reaction mixture allowed to stir at ambient temperature for 18 h. The reaction mixture was concentrated under reduced pressure and the aqueous layer acidified with aqueous HCl (1 M). The mixture was then extracted with ethyl acetate (3×20 mL) and the combined organic extracts washed with saturated aqueous sodium chloride (20 mL), dried (magnesium sulfate) and concentrated under reduced pressure to afford the title compound. MS: m/z=278.1 [M+H].

Intermediate 6

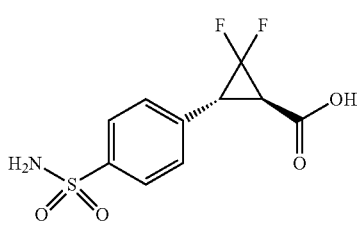 [SMILES: NS(=O)(=O)c1ccc([C@H]2[C@H](C(=O)O)C2(F)F)cc1]

(1R,3R)-2,2-Difluoro-3-(4-sulfamoylphenyl)cyclopropanecarboxylic Acid

Essentially following the procedures described in Intermediate 5, but using ethyl (1R,3R)-2,2-difluoro-3-(4-sulfamoylphenyl)cyclopropanecarboxylate (described in Intermediate 5) in place of ethyl (1S,3S)-2,2-difluoro-3-(4-sulfamoylphenyl)cyclopropanecarboxylate, the title compound was obtained. MS: m/z=278.1 [M+H].

Intermediate 7

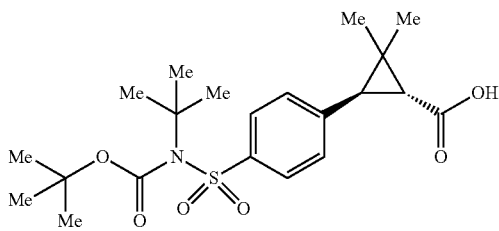 [SMILES: CC(C)(C)OC(=O)N(C(C)(C)C)S(=O)(=O)c1ccc([C@@H]2[C@@H](C(=O)O)C2(C)C)cc1]

(1R,3R)-3-{4-[(tert-Butoxycarbonyl)(tert-butyl)sulfamoyl]phenyl}-2,2-dimethylcyclopropanecarboxylic Acid Step A: Ethyl (1R,3R)-3-{4-[(tert-butoxycarbonyl)(tert-butyl)sulfamoyl]phenyl}-2,2-dimethylcyclopropanecarboxylate To a stirred solution of ethyl (1R,3R)-2,2-dimethyl-3-(4-sulfamoylphenyl)cyclopropanecarboxylate (described in Intermediate 3) (2.00 g, 6.73 mmol) in tetrahydrofuran (24 mL) at ambient temperature were added di-tert-butyl dicarbonate (7.34 g, 33.6 mmol) and DMAP (82 mg, 0.67 mmol). The resulting mixture was allowed to stir at ambient temperature for 18 h, then at 50° C. for 7 h, then allowed to cool to ambient temperature. Di-tert-butyl dicarbonate (1.50 g, 6.87 mmol) was added and the reaction mixture was allowed to stir at 50° C. for 3 h, then allowed to cool to ambient temperature. Di-tert-butyl dicarbonate (3.00 g, 13.7 mmol) and DMAP (82 mg, 0.67 mmol) were added and the reaction mixture was allowed to stir at 50° C. for 3 h, then allowed to cool to ambient temperature. The resulting mixture was concentrated under reduced pressure and the residue was purified by silica gel chromatography, eluting with a gradient of ethyl acetate:hexanes—0:100 to 30:70 to afford the title compound. MS: m/z=517.3 [M+CH$_3$CN+Na].

Step B: (1R,3R)-3-{4-[(tert-Butoxycarbonyl)(tert-butyl)sulfamoyl]phenyl}-2,2-dimethylcyclopropanecarboxylic Acid To a stirred solution of ethyl (1R,3R)-3-{4-[(tert-butoxycarbonyl)(tert-butyl)sulfamoyl]phenyl}-2,2-dimethylcyclopropanecarboxylate (2.36 g, 5.19 mmol) in tetrahydrofuran (15 mL) and methanol (15 mL) at ambient temperature was added aqueous sodium hydroxide (2.0 M, 9.47 mL, 18.9 mmol) dropwise. The resulting mixture was allowed to stir at ambient temperature for 18 h and then poured into water (50 mL). The resulting mixture was adjusted to pH=4 by addition of aqueous hydrochloric acid (1.0 M) and extracted with ethyl acetate (2×100 mL). The combined organic extracts were washed with saturated aqueous sodium chloride (40 mL), dried (sodium sulfate), filtered, and concentrated under reduced pressure to provide the title compound, which was used without further purification. MS: m/z=489.2 [M+CH$_3$CN+Na].

Intermediate 8

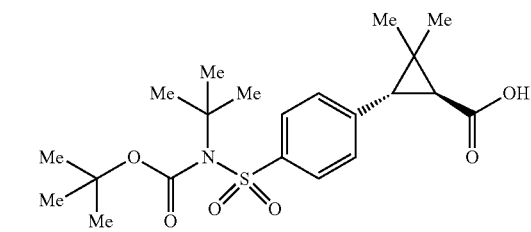 [SMILES: CC(C)(C)OC(=O)N(C(C)(C)C)S(=O)(=O)c1ccc([C@H]2[C@H](C(=O)O)C2(C)C)cc1]

(1S,3S)-3-{4-[(tert-Butoxycarbonyl)(tert-butyl)sulfamoyl]phenyl}-2,2-dimethylcyclopropanecarboxylic Acid Essentially following the procedures described in Intermediate 7, but using ethyl (1S,3S)-2,2-dimethyl-3-(4-sulfamoylphenyl)cyclopropanecarboxylate (described in Intermediate 4) in place of ethyl (1R,3R)-2,2-dimethyl-3-(4-sulfamoylphenyl)cyclopropanecarboxylate, the title compound was obtained. MS: m/z=489.4 [M+CH$_3$CN+Na].

Intermediate 9

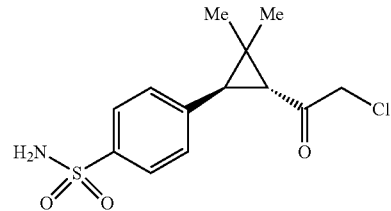 [SMILES: CC1(C)[C@H](C(=O)CCl)[C@H]1c1ccc(S(N)(=O)=O)cc1]

4-((1R,3R)-3-(2-Chloroacetyl)-2,2-dimethylcyclopropyl)benzenesulfonamide

To a solution of (1R,3R)-2,2-dimethyl-3-(4-sulfamoylphenyl)cyclopropanecarboxylic acid (Intermediate 3) (300 mg, 1.01 mmol) and chloroiodomethane (534 mg, 3.03 mmol) in THF (2 mL) was added a solution of LDA (2.0 M in THF, 2.5 mL, 5.04 mmol). The reaction mixture was allowed to stir at −78° C. for 30 min, then acetic acid (1.5 mL) was added, and the resulting mixture was allowed to warm to ambient temperature over 1 h. The mixture was poured into water (5 mL) and extracted with ethyl acetate (2×5 mL). The combined organic layers were dried (sodium sulfate), filtered, and concentrated under reduced pressure. The residue was purified by preparative TLC, eluting with ethyl acetate:hexanes—33:67, to afford the title compound. MS: m/z=302.2 [M+H].

Intermediate 10

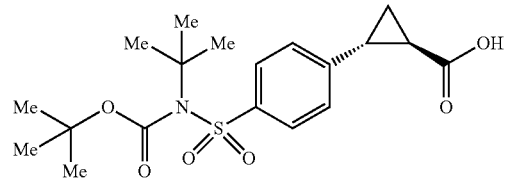 [SMILES: CC(C)(C)OC(=O)N(C(C)(C)C)S(=O)(=O)c1ccc([C@@H]2C[C@H]2C(=O)O)cc1]

(1R,2R)-2-{4-[(tert-Butoxycarbonyl)(tert-butyl)sulfamoyl]phenyl}cyclopropanecarboxylic Acid Step A: Ethyl (1R,2R)-2-{4-[(tert-butoxycarbonyl)(tert-butyl)sulfamoyl]phenyl}cyclopropanecarboxylate To a stirred solution of ethyl (1R,2R)-2-(4-sulfamoylphenyl)cyclopropanecarboxylate (described in Intermediate 1) (5.00 g, 18.6 mmol) in THF (46 mL) at ambient temperature were added di-tert-butyl dicarbonate (20.5 g, 94 mmol) and DMAP (227 mg, 1.86 mmol). The resulting mixture was allowed to stir at 50° C. for 18 h, then allowed to cool to ambient temperature. The resulting mixture was concentrated under reduced pressure and the residue was purified by silica gel chromatography, eluting with a gradient of ethyl acetate:hexanes—0:100 to 20:80 to afford the title compound. MS: m/z=426.4 [M+H].

Step B: (1R,3R)-3-{4-[(tert-Butoxycarbonyl)(tert-butyl)sulfamoyl]phenyl}-2,2-dimethylcyclopropanecarboxylic Acid To a stirred solution of ethyl (1R,2R)-2-{4-[(tert-butoxycarbonyl)(tert-butyl)sulfamoyl]phenyl}cyclopropanecarboxylate (4.0 g, 9.4 mmol) in THF (16 mL) and methanol (16 mL) at ambient temperature was added aqueous sodium hydroxide (2.0 M, 16.5 mL, 32.9 mmol) dropwise. The resulting mixture was allowed to stir at ambient temperature for 18 h, then poured into water (100 mL). The resulting mixture was adjusted to pH=4 by addition of aqueous hydrochloric acid (1.0 M) and extracted with ethyl acetate (2×200 mL). The combined organic extracts were washed with saturated aqueous sodium chloride (100 mL), dried (sodium sulfate), filtered, and concentrated under reduced pressure to provide the title compound, which was used without further purification. MS: m/z=342.3 [M-C$_4$H$_7$].

Intermediate 11

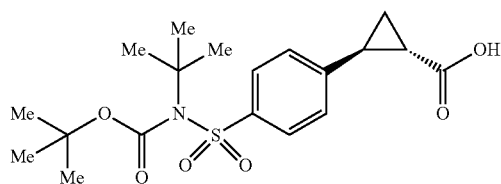 [SMILES: CC(C)(C)OC(=O)N(C(C)(C)C)S(=O)(=O)c1ccc([C@H]2C[C@@H]2C(=O)O)cc1]

(1S,2S)-2-{4-[(tert-Butoxycarbonyl)(tert-butyl)sulfamoyl]phenyl}cyclopropanecarboxylic Acid Essentially following the procedures described in Intermediate 10, but using ethyl (1S,2S)-2-{4-[(tert-butoxycarbonyl)(tert-butyl)sulfamoyl]phenyl}cyclopropanecarboxylate (described in Intermediate 2) in place of ethyl (1R,2R)-2-{4-[(tert-butoxycarbonyl)(tert-butyl)sulfamoyl]phenyl}cyclopropanecarboxylate, the title compound was obtained. MS: m/z=342.3 [M-C$_4$H$_7$].

Intermediate 12

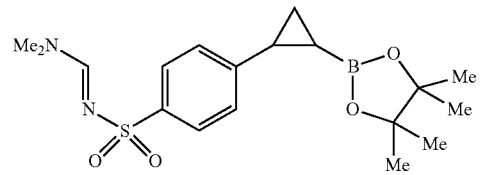 [SMILES: CN(C)/C=N/S(=O)(=O)c1ccc(C2CC2B2OC(C)(C)C(C)(C)O2)cc1]

N-[(Dimethylamino)methylidene]-4-[trans-2-(4,4,5,5-tetramethyl-1,3,2-dioxaborolan-2-yl)cyclopropyl]benzenesulfonamide Step A: 4-Bromo-N-[(dimethylamino)methylidene]benzenesulfonamide A stirred solution of 4-bromobenzenesulfonamide (5.00 g, 21.2 mmol) in N,N-dimethylformamide dimethyl acetal (113 mL) was heated at 110° C. for 18 h, then allowed to cool to ambient temperature. The resulting mixture was concentrated under reduced pressure to give the title compound in sufficient purity for use in the next step. MS: m/z=291.0 [M+H].

Step B: N-[(Dimethylamino)methylidene]-4-[(E)-2-(4,4,5,5-tetramethyl-1,3,2-dioxaborolan-2-yl)ethenyl]benzenesulfonamide To a stirred solution of 4-bromo-N-[(dimethylamino)methylidene]benzenesulfonamide (6.10 g, 21.0 mmol) in toluene (70 mL) at ambient temperature was added vinylboronic acid pinacol ester (7.11 mL, 41.9 mmol), bis(tri-tert-butylphosphine)palladium(0) (535 mg, 1.05 mmol), and triethylamine (6.42 mL, 46.1 mmol). The resulting mixture was heated at 80° C. for 18 h, then poured into water (100 mL) and extracted with ethyl acetate (2×200 mL). The combined organic extracts were washed with saturated aqueous sodium chloride (100 mL), dried (sodium sulfate), filtered, and concentrated under reduced pressure. The residue was purified by silica gel chromatography, eluting with a gradient of ethyl acetate:hexanes—0:100 to 30:70 to afford the title compound. MS: m/z=365.3 [M+H].

Step C: N-[(Dimethylamino)methylidene]-4-[trans-2-(4,4,5,5-tetramethyl-1,3,2-dioxaborolan-2-yl)-3-(trimethylsilyl)cyclopropyl]benzenesulfonamide To a stirred solution of N-[(dimethylamino)methylidene]-4-[(E)-2-(4,4,5,5-tetramethyl-1,3,2-dioxaborolan-2-yl)ethenyl]benzenesulfonamide (6.00 g, 16.5 mmol) in tetrahydrofuran (82 mL) at ambient temperature was added palladium(II) acetate (924 mg, 4.12 mmol) and (trimethylsilyl)diazomethane (2.0 M in diethyl ether, 24.7 mL, 49.4 mmol), sequentially. The reaction mixture was allowed to stir at ambient temperature for 18 h, then acetic acid (12 mL) was added and the resulting mixture was poured into water (200 mL) and extracted with dichloromethane (3×200 mL). The combined organic extracts were dried (sodium sulfate), filtered, and concentrated under reduced pressure. The residue was purified by silica gel chromatography, eluting with a gradient of ethyl acetate:hexanes—10:90 to 60:40 to afford the title compound. MS: m/z=451.3 [M+H].

Step D: N-[(Dimethylamino)methylidene]-4-[trans-2-(4,4,5,5-tetramethyl-1,3,2-dioxaborolan-2-yl)cyclopropyl]benzenesulfonamide To a stirred solution of N-[(dimethylamino)methylidene]-4-[trans-2-(4,4,5,5-tetramethyl-1,3,2-dioxaborolan-2-yl)-3-(trimethylsilyl)cyclopropyl]benzenesulfonamide (1.25 g, 2.77 mmol) in dichloromethane (22 mL) at 0° C. was added trifluoromethanesulfonic acid (0.801 mL, 9.02 mmol). The reaction mixture was allowed to warm to ambient temperature and allowed to stir for 2 h, then poured into saturated aqueous sodium bicarbonate (50 mL), and extracted with dichloromethane (2×100 mL). The combined organic extracts were dried (sodium sulfate), filtered, and concentrated under reduced pressure. The residue was purified by silica gel chromatography, eluting with a gradient of methanol:dichloromethane—0:100 to 4:96 to afford the title compound. MS: m/z=379.3 [M+H].

Intermediate 13

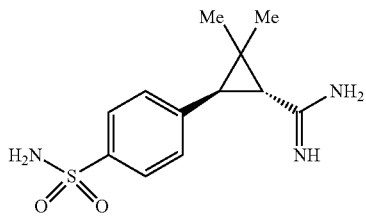 [SMILES: CC1(C)[C@H](C(=N)N)[C@H]1c1ccc(S(N)(=O)=O)cc1]

(1R,3R)-2,2-Dimethyl-3-(4-sulfamoylphenyl)cyclopropanecarboximidamide

Step A: (1R,3R)-2,2-Dimethyl-3-(4-sulfamoylphenyl)cyclopropanecarboxamide

To a stirred solution of (1R,3R)-2,2-dimethyl-3-(4-sulfamoylphenyl)cyclopropanecarboxylic acid (Intermediate 3) (850 mg, 3.16 mmol) in THF (10 mL) was added 1,1'-carbonyldiimidazole (614 mg, 3.79 mmol) and the resulting mixture was stirred at ambient temperature for 1 h. Aqueous ammonium hydroxide (28% solution, 8.8 mL, 130 mmol) was added and the reaction mixture was stirred at ambient temperature for 12 h. The mixture was concentrated under reduced pressure to remove THF and the residual mixture was adjusted to pH=3 by addition of 1 M aqueous hydrochloric acid. The aqueous layer was extracted with ethyl acetate (3×10 mL) and the combined organic extracts were washed with saturated aqueous potassium carbonate (2×10 mL), dried (sodium sulfate), filtered, and the solvent evaporated under reduced pressure to afford the title compound in sufficient purity for use in the next step. MS: m/z=269.1 [M+H].

Step B: 4-[(1R,3R)-3-Cyano-2,2-dimethylcyclopropyl]-N-[(dimethylamino)methylidene]benzenesulfonamide To a stirred solution of (1R,2R)-2-(4-sulfamoylphenyl)cyclopropanecarboxamide (500 mg, 1.86 mmol) in N,N-dimethylformamide (8 mL) at ambient temperature was added thionyl chloride (3.3 g, 27 mmol) dropwise and the resulting solution was allowed to stir for 1 h at ambient temperature. The reaction mixture was diluted with water (10 mL) and extracted with ethyl acetate (3×10 mL). The combined organic extracts were washed with saturated aqueous sodium chloride (25 mL), dried (sodium sulfate), and concentrated under reduced pressure. The residue was purified by silica gel chromatography, eluting with ethyl acetate, to afford the title compound. MS: m/z=306.1 [M+H].

Step C: Ethyl (1R,3R)-3-(4-{[(dimethylamino)methylidene]sulfamoyl}phenyl)-2,2-dimethylcyclopropanecarboximidoate A solution of 4-[(1R,3R)-3-cyano-2,2-dimethylcyclopropyl]-N-[(dimethylamino)methylidene]benzenesulfonamide (180 mg, 0.59 mmol) in ethanol (10 mL) at 0° C. was saturated with hydrogen chloride (g) and the resulting mixture was allowed to stir at ambient temperature for 4 h. The reaction mixture was concentrated under reduced pressure to afford the title compound in sufficient purity for use in the next step. MS: m/z=352.1 [M+H].

Step D: (1R,3R)-2,2-Dimethyl-3-(4-sulfamoylphenyl)cyclopropanecarboximidamide To a mixture of ethyl (1R,3R)-3-(4-{[(dimethylamino)methylidene]sulfamoyl}phenyl)-2,2-dimethylcyclopropanecarboximidoate (200 mg, 0.57 mmol) and EtOH (5 mL) at 0° C. was added a saturated solution of ammonia in methanol (5 mL). The reaction mixture was allowed to stir at 50° C. for 12 h and was then concentrated under reduced pressure to afford the title compound in sufficient purity for use in the next step. MS: m/z=268.0 [M+H].

Example 1

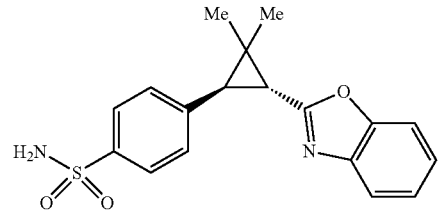 [SMILES: CC1(C)[C@H](c2ccc(S(N)(=O)=O)cc2)[C@H]1c1nc2ccccc2o1]

4-[(1R,3R)-3-(1,3-Benzoxazol-2-yl)-2,2-dimethylcyclopropyl]benzenesulfonamide

To a stirred solution of (1R,3R)-2,2-dimethyl-3-(4-sulfamoylphenyl)cyclopropanecarboxylic acid (Intermediate 3) (4.00 g, 14.9 mmol) in dichloromethane (70 mL) and DMF (4 drops) was added, dropwise, a solution of oxalyl chloride (2.0 M in dichloromethane, 7.43 mL, 14.9 mmol). The resulting mixture was allowed to stir at ambient temperature for 1 h then an additional solution of oxalyl chloride (2.0 M in dichloromethane, 7.43 mL, 14.9 mmol) was added dropwise. The reaction mixture was allowed to stir for 30 min and then toluene (5 mL) was added and the mixture was concentrated under reduced pressure. The residue was dissolved in 1,4-dioxane (65 mL), 2-aminophenol (1.78 g, 16.3 mmol) was added, and the reaction mixture was heated at reflux for 18 h then allowed to cool to ambient temperature. Toluene-4-sulfonic acid monohydrate (2.83 g, 14.9 mmol) and toluene (24 mL) were added and the resulting mixture was heated at reflux for 24 h, using a Dean-Stark trap, then allowed to cool to ambient temperature. The mixture was poured into saturated aqueous sodium bicarbonate (100 mL) and extracted with ethyl acetate (2×200 mL). The combined organic extracts were dried (sodium sulfate), filtered, and concentrated under reduced pressure. The residue was purified by silica gel chromatography, eluting with a gradient of ethyl acetate:hexanes—0:100 to 40:60 to afford the title compound. MS: m/z=343.1 [M+H]. $^1$H NMR (500 MHz, DMSO-$d_6$): δ 7.77 (d, J=8.5 Hz, 2H); 7.69-7.66 (m, 2H), 7.55 (d, J=8.5 Hz, 2H); 7.35-7.33 (m, 2H); 7.32 (s, 2H); 2.98 (d, J=6.3 Hz, 1H); 2.91 (d, J=6.3 Hz, 1H); 1.27 (s, 3H); 0.99 (s, 3H).

Example 2

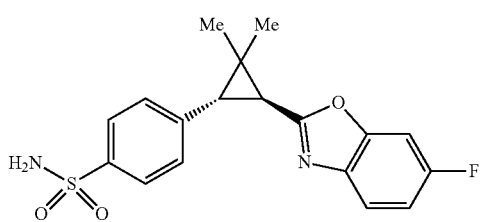 [SMILES: CC1(C)[C@@H](c2ccc(S(N)(=O)=O)cc2)[C@@H]1c1nc2ccc(F)cc2o1]

4-[(1S,3S)-3-(6-Fluoro-1,3-benzoxazol-2-yl)-2,2-dimethylcyclopropyl]benzenesulfonamide A stirred mixture of (1S,3S)-2,2-dimethyl-3-(4-sulfamoylphenyl)cyclopropanecarboxylic acid (Intermediate 4) (50 mg, 0.19 mmol) and 2-amino-5-fluorophenol (71 mg, 0.56 mmol) in trimethylsilyl polyphosphate (1.0 mL) was heated at 120° C. for 1 h then allowed to cool to ambient temperature. The mixture was diluted with MeOH and purified by preparative HPLC, eluting with a gradient of acetonitrile:water:trifluoroacetic acid—10:90:0.1 to 90:10:0.1. The product-containing fractions were poured into saturated aqueous sodium bicarbonate (40 mL) and the resulting mixture was extracted with ethyl acetate (2×70 mL). The combined organic extracts were dried (sodium sulfate), filtered, and concentrated under reduced pressure. The residue was purified by silica gel chromatography, eluting with a gradient of ethyl acetate:hexanes—0:100 to 80:20 to afford the title compound. MS: m/z=361.0 [M+H]. $^1$H NMR (500 MHz, DMSO-$d_6$): δ 7.77 (d, J=8.2 Hz, 2H); 7.76-7.70 (m, 2H), 7.54 (d, J=8.0 Hz, 2H); 7.32 (s, 2H); 7.21 (dd, J=9.0, 2.5 Hz, 1H); 2.96 (d, J=6.2 Hz, 1H); 2.91 (d, J=6.2 Hz, 1H); 1.26 (s, 3H); 0.98 (s, 3H).

Example 3

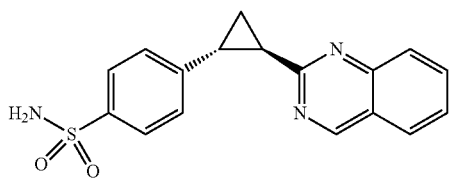 [SMILES: NS(=O)(=O)c1ccc([C@@H]2C[C@H]2c2ncc3ccccc3n2)cc1]

4-[(1R,2R)-2-(Quinazolin-2-yl)cyclopropyl]benzenesulfonamide

To a solution of (1R,2R)-2-(4-sulfamoylphenyl)cyclopropanecarboxylic acid (Intermediate 1) (59 mg, 0.25 mmol) in DMSO (2.40 mL) at ambient temperature was added HATU (107 mg, 0.281 mmol), triethylamine (0.137 mL, 0.980 mmol), and 2-(aminomethyl)aniline (34.7 mg, 0.284 mmol) sequentially. The reaction mixture was allowed to stir for 30 min. Acetic acid (2.80 mL, 48.9 mmol) was added, the reaction mixture warmed to 90° C. and allowed to stir for 18 h, and concentrated under reduced pressure. The residue was co-evaporated with hexane (2×) and concentrated under a stream of nitrogen. The residue was taken up in dichloromethane (2.5 mL), treated with Dess-Martin periodinane (108 mg, 0.255 mmol), and allowed to stir for 15 min. The reaction mixture was poured into a mixture of saturated aqueous sodium bicarbonate (5 mL), saturated aqueous sodium sulfite (5 mL), and saturated aqueous sodium thiosulfate (5 mL) and extracted with ethyl acetate (3×25 mL). The combined organic extracts were washed with saturated aqueous sodium chloride (15 mL), dried (sodium sulfate), filtered, and concentrated under reduced pressure. The residue was purified by silica gel chromatography, eluting with a gradient of ethyl acetate:hexanes—10:90 to 50:50 to afford the title compound. MS: m/z=326.2 [M+H]. $^1$H NMR (500 MHz, DMSO-$d_6$): δ 9.54 (s, 1H); 8.12 (d, J=8.1 Hz, 1H); 7.99 (d, J=8.0 Hz, 1H); 7.91 (d, J=8.2 Hz, 1H); 7.75 (d, J=8.0 Hz, 2H); 7.69 (t, J=7.6 Hz, 1H); 7.46 (d, J=7.9 Hz, 2H); 7.31 (s, 2H); 2.74 (s, 2H); 1.94 (s, 1H); 1.73 (s, 1H).

Example 4

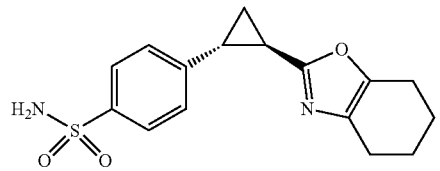 [SMILES: NS(=O)(=O)c1ccc([C@@H]2C[C@H]2c2nc3c(o2)CCCC3)cc1]

4-[(1R,2R)-2-(4,5,6,7-Tetrahydro-1,3-benzoxazol-2-yl)cyclopropyl]benzenesulfonamide To a solution of (1R,2R)-2-(4-sulfamoylphenyl)cyclopropanecarboxylic acid (Intermediate 1) (103 mg, 0.428 mmol) in dichloromethane (2 mL) and dimethylsulfoxide (0.2 mL) at ambient temperature was added N-methylmorpholine (0.094 mL, 0.86 mmol), HATU (183 mg, 0.482 mmol), and 2-aminocyclohexanone hydrochloride (99.2 mg, 0.663 mmol) sequentially. The reaction mixture was allowed to stir for 30 min, poured into saturated aqueous ammonium chloride (7 mL), and the mixture extracted with ethyl acetate (3×15 mL). The combined organic extracts were washed with saturated aqueous ammonium chloride (2×15 mL) and saturated aqueous sodium chloride (15 mL), dried (magnesium sulfate), filtered, and concentrated under reduced pressure. The residue was purified by preparative HPLC, eluting with a gradient of acetonitrile:water:trifluoroacetic acid—5:95:0.1 to 70:30:0.1. The product-containing fractions were made basic with saturated aqueous sodium bicarbonate (5 mL) and extracted with ethyl acetate (2×15 mL). The combined organic extracts were washed with saturated aqueous sodium chloride (10 mL), dried (magnesium sulfate), and concentrated under reduced pressure. The residue was suspended in dioxane (4 mL), treated with phosphorus oxychloride (0.319 mL, 3.42 mmol), warmed to 70° C., and allowed to stir for 13 h. The reaction mixture was allowed to cool to ambient temperature and was poured into cold saturated aqueous sodium bicarbonate (20 mL), and extracted with ethyl acetate (3×30 mL). The combined organic extracts were washed with saturated aqueous sodium chloride (15 mL), dried (magnesium sulfate), filtered, and the concentrated under reduced pressure. The residue was purified by preparative HPLC, eluting with a gradient of acetonitrile:water:trifluoroacetic acid—10:90:0.1 to 85:15:0.1. The product-containing fractions were made basic with saturated aqueous sodium bicarbonate (5 mL) and extracted with ethyl acetate (3×20 mL). The combined organic extracts were washed with saturated aqueous sodium chloride (10 mL), dried (magnesium sulfate), filtered, and concentrated under reduced pressure to afford the title compound. MS: m/z=319.3 [M+H]. $^1$H NMR (500 MHz, DMSO-d$_6$): δ 7.71 (d, J=8.2 Hz, 2H); 7.38 (d, J=8.2 Hz, 2H); 7.29 (s, 2H); 2.54 (d, J=6.9 Hz, 3H); 2.39-2.43 (m, 1H); 2.37-2.38 (m, 2H); 1.74-1.77 (m, 2H); 1.69-1.71 (m, 2H); 1.62-1.66 (m, 1H); 1.57 (dt, J=9.0, 5.5 Hz, 1H).

Example 5

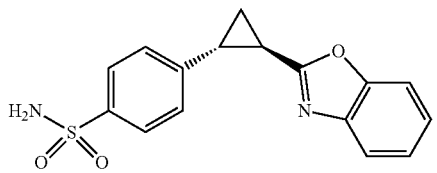 [SMILES: NS(=O)(=O)c1ccc([C@@H]2C[C@H]2c2nc3ccccc3o2)cc1]

4-[(1R,2R)-2-(1,3-Benzoxazol-2-yl)cyclopropyl]benzenesulfonamide

Step A: (1R,2R)—N-(2-Hydroxyphenyl)-2-(4-sulfamoylphenyl)cyclopropanecarboxamide To a stirred solution of (1R,2R)-2-(4-sulfamoylphenyl)cyclopropanecarboxylic acid (Intermediate 1) (63 mg, 0.26 mmol) in DMF (1 mL) were added 2-aminophenol (37 mg, 0.34 mmol), EDC (65 mg, 0.34 mmol), HOAt (46 mg, 0.34 mmol), and triethylamine (0.11 mL, 0.78 mmol) sequentially. The resulting mixture was allowed to stir at ambient temperature for 18 h then diluted with ethyl acetate (10 mL), filtered, and concentrated under reduced pressure. The residue was purified by silica gel chromatography, eluting with a gradient of dichloromethane:methanol—100:0 to 90:10 to afford the title compound. MS: m/z=333.0 [M+H].

Step B: 4-[(1R,2R)-2-(1,3-Benzoxazol-2-yl)cyclopropyl]benzenesulfonamide

To a stirred solution of (1R,2R)—N-(2-hydroxyphenyl)-2-(4-sulfamoylphenyl)cyclopropanecarboxamide (29 mg, 0.087 mmol) in 1,4-dioxane (1.4 mL) and toluene (0.7 mL) was added toluene-4-sulfonic acid monohydrate (17 mg, 0.089 mmol) and the resulting mixture was heated in a microwave reactor at 120° C. for 6 h. The resulting mixture was cooled to ambient temperature and concentrated under reduced pressure. The residue was purified by silica gel chromatography, eluting with a gradient of dichloromethane:methanol—100:0 to 90:10 to afford the title compound. MS: m/z=315.1 [M+H]. $^1$H NMR (500 MHz, DMSO-d$_6$): δ 7.74 (d, J=8.4 Hz, 2H); 7.66-7.63 (m, 2H), 7.45 (d, J=8.4 Hz, 2H); 7.35-7.32 (m, 2H); 7.30 (s, 2H); 2.98 (dt, J=10.1, 4.8 Hz, 1H); 2.68 (dt, J=9.0, 4.8 Hz, 1H); 1.90-1.85 (m, 1H); 1.80-1.75 (m, 1H).

Example 6

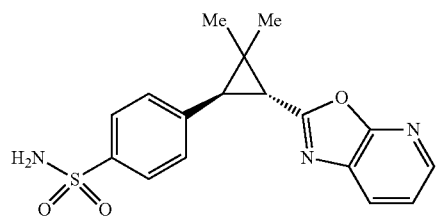 [SMILES: CC1(C)[C@H](c2ccc(S(N)(=O)=O)cc2)[C@H]1c1nc2cccnc2o1]

4-[(1R,3R)-2,2-Dimethyl-3-([1,3]oxazolo[5,4-b]pyridin-2-yl)cyclopropyl]benzenesulfonamide To a stirred solution of (1R,3R)-3-{4-[(tert-butoxycarbonyl)(tert-butyl)sulfamoyl]phenyl}-2,2-dimethylcyclopropanecarboxylic acid (Intermediate 7) (70 mg, 0.16 mmol) in dichloromethane (1.5 mL) were added triethylamine (0.090 mL, 0.65 mmol) and 1-chloro-N,N,2-trimethylprop-1-en-1-amine (0.024 mL, 0.18 mmol) sequentially and the resulting mixture was allowed to stir at ambient temperature for 30 min. 3-Aminopyridin-2-ol (20 mg, 0.18 mmol) was added and the reaction mixture was allowed to stir at 40° C. for 3 h then allowed to cool. A solution of hexachloroethane (97 mg, 0.41 mmol), triphenylphosphine (129 mg, 0.49 mmol), and triethylamine (0.17 mL, 1.22 mmol) in dichloromethane (1 mL) was allowed to stir for 10 min then added to the cooled reaction mixture. The resulting mixture was heated at 45° C. for 3 h, allowed to cool to ambient temperature, and concentrated to dryness under reduced pressure. The residue was dissolved in dichloromethane (2 mL) and trifluoroacetic acid (0.5 mL) and the resulting mixture was allowed to stir at ambient temperature for 3 h then partitioned between saturated aqueous sodium bicarbonate (40 mL) and ethyl acetate (80 mL). The organic extract was washed with saturated aqueous sodium chloride (30 mL), dried (sodium sulfate), filtered, and concentrated under reduced pressure. The residue was purified by silica gel chromatography, eluting with a gradient of dichloromethane:methanol—100:0 to 90:10 to provide partial purification. Further purification was achieved by silica gel chromatography, eluting with a gradient of ethyl acetate:hexanes—0:100 to 70:30 to afford the title compound. MS: m/z=344.1 [M+H]. $^1$H NMR (500 MHz, DMSO-d$_6$): δ 8.30 (dd, J=4.8, 1.4 Hz, 1H); 8.14 (dd, J=7.9, 1.4 Hz, 1H); 7.78 (d, J=8.1 Hz, 2H), 7.56 (d, J=8.1 Hz, 2H); 7.44 (dd, J=7.9, 5.0 Hz, 1H); 7.32 (s, 2H); 3.02 (d, J=6.0 Hz, 1H); 2.97 (d, J=6.0 Hz, 1H); 1.30 (s, 3H); 1.00 (s, 3H).

Example 7

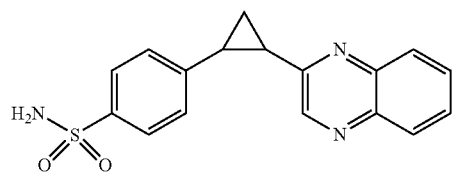 [SMILES: NS(=O)(=O)c1ccc(C2CC2c2cnc3ccccc3n2)cc1]

4-[trans-2-(Quinoxalin-2-yl)cyclopropyl]benzene-sulfonamide

To a stirred mixture of N-[(dimethylamino)methylidene]-4-[trans-2-(4,4,5,5-tetramethyl-1,3,2-dioxaborolan-2-yl)cyclopropyl]benzenesulfonamide (Intermediate 12) (30 mg, 0.079 mmol) and 2-bromoquinoxaline (29 mg, 0.139 mmol) in toluene (0.79 mL) were added cataCXium® A-Pd-G2 [2'-(dimethylamino)-2-biphenyl-palladium(II)-chloride di(1-adamantyl)-n-butylphosphine complex] (5.3 mg, 0.0079 mmol) and potassium phosphate tribasic (1 M in water, 0.24 mL, 0.24 mmol) sequentially. The resulting mixture was allowed to stir at 100° C. for 18 h then allowed to cool to ambient temperature. Ethyl acetate (3 mL) and water (0.5 mL) were added and the mixture was filtered through celite. The filtrate was concentrated to remove organic solvent and the residue was treated with hydrazine hydrate (50-60%, 1 mL) and ethanol (0.5 mL), sonicated for 90 min, then concentrated to dryness. The residue was purified by preparative HPLC, eluting with a gradient of acetonitrile:water:trifluoroacetic acid—10:90:0.1 to 95:5:0.1. The product-containing fractions were concentrated under reduced pressure to give the title compound. MS: m/z=326.2 [M+H]. $^1$H NMR (500 MHz, DMSO-$d_6$): δ 9.02 (s, 1H); 8.05 (d, J=8.3 Hz, 1H); 8.00 (d, J=8.3 Hz, 1H); 7.83 (m, 1H); 7.82-7.70 (m, 3H); 7.45 (d, J=8.0 Hz, 2H); 7.30 (s, 2H); 2.86 (m, 1H); 2.74 (m, 1H); 1.97 (m, 1H); 1.78 (m, 1H).

Example 8

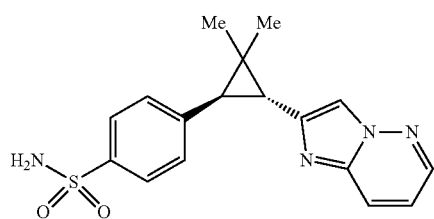 [SMILES: CC1(C)[C@H](c2ccc(S(N)(=O)=O)cc2)[C@H]1c1cn2ncccc2n1]

4-((1R,3R)-3-(Imidazo[1,2-b]pyridazin-2-yl)-2,2-dimethylcyclopropyl)benzenesulfonamide To a solution of 4-((1R,3R)-3-(2-chloroacetyl)-2,2-dimethylcyclopropyl)benzenesulfonamide (Intermediate 9) (50 mg, 0.166 mmol) in ethanol (1 mL) was added sodium bicarbonate (27.8 mg, 0.331 mmol) and pyridazin-3-amine (18.9 mg, 0.199 mmol) and the stirred mixture was heated at 80° C. in a microwave reactor. The reaction mixture was filtered, and the filtrate was purified by preparative HPLC, eluting with a gradient of acetonitrile:water:trifluoroacetic acid—5:95:0.1 to 35:65:0.1. The product-containing fractions were concentrated under reduced pressure to give the title compound. MS: m/z=343.1 [M+H]. $^1$H NMR (400 MHz, CD$_3$OD): δ 8.77 (d, J=3.2 Hz, 1H); 8.38 (s, 1H); 8.25 (d, J=9.2 Hz, 2H); 7.88 (d, J=8.4 Hz, 2H); 7.66 (dd, J=4.8, 9.6 Hz, 1H); 7.51 (d, 8.4 Hz, 2H); 2.83 (d, 6.0 Hz, 1H); 2.69 (d, 6.0 Hz, 1H); 1.20 (s, 3H); 1.05 (s, 3H).

Example 9

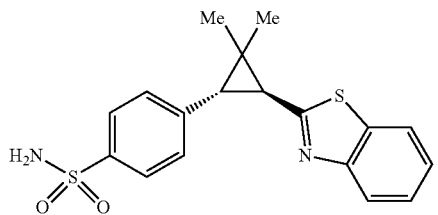 [SMILES: CC1(C)[C@@H](c2ccc(S(N)(=O)=O)cc2)[C@@H]1c1nc2ccccc2s1]

4-((1S,3S)-3-(Benzodithiazol-2-yl)-2,2-dimethylcyclopropyl)benzenesulfonamide

To a suspension of (1S,3S)-2,2-dimethyl-3-(4-sulfamoylphenyl)cyclopropanecarboxylic acid (Intermediate 4) (250 mg, 0.928 mmol) in polyphosphoric acid (2.4 mL) was added 2-aminobenzenethiol (232 mg, 1.86 mmol). The stirred mixture was heated at 70° C. for 30 min. The reaction mixture was treated with water (10 mL), and the resulting mixture was extracted with ethyl acetate (3×10 mL). The combined organic extracts were concentrated under reduced pressure. The residue was purified by preparative HPLC, eluting with a gradient of acetonitrile:water:ammonium hydroxide—37:63:0.05 to 67:33:0.05. The product-containing fractions were concentrated under reduced pressure to give the title compound. MS: m/z=359.1 [M+H]. $^1$H NMR (400 MHz, CD$_3$OD): δ 7.90 (m, 2H); 7.86 (d, J=8.4 Hz, 2H); 7.48 (d, J=8.4 Hz, 2H); 7.46 (d, J=7.2 Hz, 1H); 7.38 (dd, J=7.2, 8.0 Hz, 1H); 3.11 (d, J=6.4 Hz, 1H); 2.96 (d, J=6.4 Hz, 1H); 1.24 (s, 3H); 1.03 (s, 3H).

Example 10

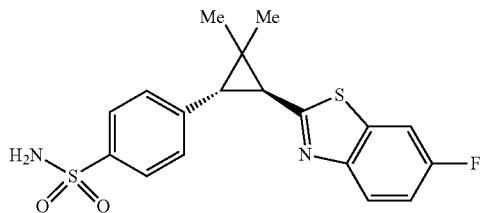 [SMILES: CC1(C)[C@@H](c2ccc(S(N)(=O)=O)cc2)[C@@H]1c1nc2ccc(F)cc2s1]

4-((1S,3S)-3-(6-Fluorobenzo[d]thiazol-2-yl)-2,2-dimethylcyclopropyl)benzenesulfonamide Step A: (1S,3S)—N-(4-Fluoro-2-iodophenyl)-2,2-dimethyl-3-(4-sulfamoylphenyl)cyclopropane-1-carboxamide To a stirred solution of (1S,3S)-2,2-dimethyl-3-(4-sulfamoylphenyl)cyclopropanecarboxylic acid (Intermediate 4) (200 mg, 0.743 mmol) in DMF (8 mL) was added HATU (339 mg, 0.891 mmol) and N,N-diisopropylethylamine (0.39 mL, 2.2 mmol), and the mixture was allowed to stir at 0° C. for 20 min. 4-Fluoro-2-iodoaniline (264 mg, 1.11 mmol) was added, and the reaction mixture was allowed to stir at ambient temperature for 16 h. Water (30 mL) was added, and the mixture was extracted with ethyl acetate (3×50 mL). The combined organic extracts were washed with water (2×50 mL), then saturated aqueous sodium chloride (100 mL), dried (sodium sulfate), filtered, and concentrated under reduced pressure. The residue was purified by preparative TLC, eluting with ethyl acetate: hexanes—50:50, to afford the title compound. MS: m/z=489.0 [M+H].

Step B: 4-((1S,3S)-3-(6-Fluorobenzo[d]thiazol-2-yl)-2,2-dimethylcyclopropyl)benzenesulfonamide A stirred mixture of (1S,3S)—N-(4-fluoro-2-iodophenyl)-2,2-dimethyl-3-(4-sulfamoylphenyl)cyclopropanecarboxamide (80 mg, 0.164 mmol), cuprous iodide (6.2 mg, 0.033 mmol), and sodium sulfide nonahydrate (118 mg, 0.491 mmol) in DMF (2 mL) was heated at 80° C. for 16 h. The reaction mixture was cooled to ambient temperature, 37.0 wt % aqueous hydrochloric acid (0.40 mL, 4.9 mmol) was added, and the mixture was allowed to stir at ambient temperature for 20 h. Saturated aqueous sodium bicarbonate solution was added to adjust the mixture to pH=9, water (20 mL) was added, and the mixture was extracted with ethyl acetate (3×30 mL). The combined organic extracts were washed with saturated aqueous sodium chloride (50 mL), dried (sodium sulfate), filtered, and concentrated under reduced pressure. The residue was purified by preparative HPLC, eluting with a gradient of acetonitrile:water:ammonium hydroxide—37:63:0.05 to 67:33:0.05. The product-containing fractions were concentrated under reduced pressure to give the title compound. MS: m/z=377.1 [M+H]. $^1$H NMR (400 MHz, CD$_3$OD): δ 7.90 (m, 1H); 7.88 (d, J=8.4 Hz, 2H); 7.71 (dd, J=2.4 Hz, 8.4 Hz, 1H); 7.50 (d, J=8.4 Hz, 2H); 7.27 (m, 1H); 3.13 (d, J=6.4 Hz, 1H); 2.97 (d, J=6.4 Hz, 1H); 1.27 (s, 3H); 1.05 (s, 3H).

Example 11

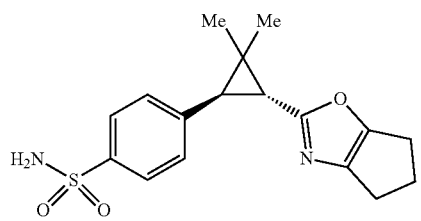 [SMILES: CC1(C)[C@H](c2ccc(S(N)(=O)=O)cc2)[C@H]1c1nc2c(o1)CCC2]

4-[(1R,3R)-3-(5,6-Dihydro-4H-cyclopenta[d][1,3]oxazol-2-yl)-2,2-dimethylcyclopropyl]benzenesulfonamide Step A: tert-Butyl tert-butyl[(4-{(1R,3R)-2,2-dimethyl-3-[(2-oxocyclopentyl)carbamoyl]cyclopropyl}phenyl)sulfonyl]carbamate To a stirred solution of (1R,3R)-3-{4-[(tert-butoxycarbonyl)(tert-butyl)sulfamoyl]phenyl}-2,2-dimethylcyclopropanecarboxylic acid (Intermediate 7) (200 mg, 0.47 mmol) in dichloromethane (3 mL) and DMF (0.3 mL) were added HATU (214 mg, 0.562 mmol), 4-methylmorpholine (0.16 mL, 1.5 mmol), and 2-aminocyclopentanone (70 mg, 0.71 mmol), sequentially, and the mixture was allowed to stir at ambient temperature for 2 h. Saturated aqueous ammonium chloride (20 mL) was added, and the mixture was extracted with ethyl acetate (70 mL). The organic extract was washed with saturated aqueous sodium bicarbonate (30 mL), then saturated aqueous sodium chloride (30 mL), then dried (sodium sulfate), filtered, and concentrated under reduced pressure. The residue was purified by silica gel chromatography, eluting with a gradient of ethyl acetate:hexanes—0:100 to 100:0 to afford the title compound. MS: m/z=507.3 [M+H].

Step B: 4-[(1R,3R)-3-(5,6-Dihydro-4H-cyclopenta[d][1.3]oxazol-2-yl)-2,2-dimethylcyclopropyl]benzenesulfonamide A mixture of triphenylphosphine (211 mg, 0.81 mmol) and carbon tetrachloride (0.27 mL, 2.80 mmol) in dichloromethane (2.7 mL) was allowed to stir at ambient temperature for 40 min. To the resulting mixture were added triethylamine (0.39 mL, 2.80 mmol) and tert-butyl tert-butyl [(4-{(1R,3R)-2,2-dimethyl-3-[(2-oxocyclopentyl)carbamoyl]cyclopropyl}phenyl)sulfonyl]carbamate (136 mg, 0.27 mmol) and the reaction mixture was heated at 50° C. for 4 h. The reaction mixture was cooled to ambient temperature and poured into ethyl acetate (50 mL) and the mixture was washed with saturated aqueous sodium bicarbonate (20 mL), then saturated aqueous sodium chloride (20 mL), then dried (sodium sulfate), filtered, and concentrated under reduced pressure. The residue was purified by silica gel chromatography, eluting with a gradient of ethyl acetate:hexanes—0:100 to 50:50 to afford tert-butyl tert-butyl({4-[(1R,3R)-3-(5,6-dihydro-4H-cyclopenta[d][1,3]oxazol-2-yl)-2,2-dimethylcyclopropyl]phenyl}sulfonyl)carbamate, which was dissolved in dichloromethane (2.5 mL) and treated with trifluoroacetic acid (0.6 mL, 7.8 mmol). The resulting mixture was allowed to stir at ambient temperature for 2 h, then partitioned between ethyl acetate (70 mL) and saturated aqueous sodium bicarbonate (30 mL), then saturated aqueous sodium chloride (20 mL), then dried (sodium sulfate), filtered, and concentrated under reduced pressure. The residue was purified by silica gel chromatography, eluting with a gradient of ethyl acetate:hexanes—0:100 to 100:0 to afford the title compound. MS: m/z=333.1 [M+H]. $^1$H NMR (500 MHz, DMSO-d$_6$): δ 7.75 (d, J=8.0 Hz, 2H); 7.48 (d, J=8.0 Hz, 2H); 7.31 (s, 2H); 2.72 (m, 1H); 2.65-2.66 (m, 3H); 2.46-2.47 (m, 4H); 1.20 (s, 3H); 0.91 (s, 3H).

Example 12

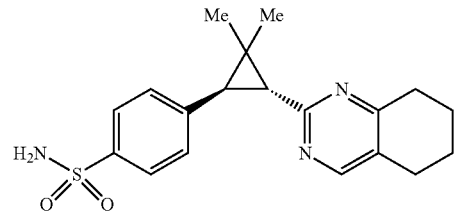 [SMILES: CC1(C)[C@H](c2ccc(S(N)(=O)=O)cc2)[C@H]1c1ncc2c(n1)CCCC2]

4-[(R,3R)-2,2-Dimethyl-3-(5,6,7,8-tetrahydroquinazolin-2-yl)cyclopropyl]benzenesulfonamide To a solution of (2E)-2-[(dimethylamino)methylene]cyclohexanone (20 mg, 0.13 mmol) in ethanol (1 mL) at ambient temperature were added (1R,3R)-2,2-dimethyl-3-(4-sulfamoylphenyl)cyclopropanecarboximidamide (Intermediate 13) (52 mg, 0.20 mmol) and sodium methoxide (10.6 mg, 0.20 mmol). The stirred reaction mixture was heated at 80° C. for 12 h, allowed to cool to ambient temperature, and was then purified by preparative HPLC, eluting with a gradient of acetonitrile:water:ammonium hydroxide—27:73:0.05 to 57:43:0.05, and the product-containing fractions were concentrated under reduced pressure to afford the title compound. MS: m/z=358.0 [M+H]. $^1$H NMR (400 MHz, CD$_3$OD): δ 8.36 (s, 1H); 7.84 (d, J=8.4 Hz, 2H); 7.43 (d, J=8.2 Hz, 2H); 3.11 (d, J=6.2 Hz, 1H); 2.85 (t, J=6.1 Hz, 2H); 2.76 (t, J=6.2 Hz, 2H); 2.66 (d, J=6.2 Hz, 1H); 1.80-1.95 (m, 4H); 1.19 (s, 3H); 1.00 (s, 3H).

Example 13

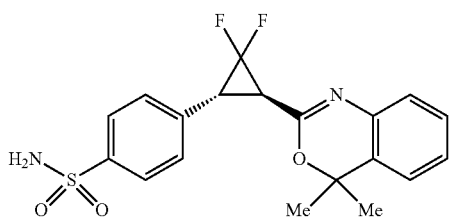 [SMILES: CC1(C)OC([C@H]2[C@H](c3ccc(S(N)(=O)=O)cc3)C2(F)F)=Nc2ccccc21]

4-[(1R,3R)-3-(4,4-Dimethyl-4H-3,1-benzoxazin-2-yl)-2,2-difluorocyclopropyl]benzenesulfonamide Step A: (1R,3R)-2,2-Difluoro-N-[2-(2-hydroxypropan-2-yl)phenyl]-3-(4-sulfamoylphenyl)cyclopropanecarboxamide To a stirred solution of (1R,3R)-2,2-difluoro-3-(4-sulfamoylphenyl)cyclopropanecarboxylic acid (Intermediate 6) (100 mg, 0.36 mmol) in 1,4-dioxane (0.72 mL) was added 1,1'-carbonyldiimidazole (35 mg, 0.22 mmol) and the mixture was stirred at ambient temperature for 3 h. To the resulting mixture was added 2-(2-aminophenyl)propan-2-ol (60 mg, 0.40 mmol) and the stirred reaction mixture was heated at 50° C. for 6 h. The reaction mixture was allowed to cool and was then concentrated under reduced pressure. The residue was diluted with water (10 mL), extracted with ethyl acetate (2×20 mL), and the combined organic extracts were dried (magnesium sulfate), filtered, and concentrated under reduced pressure to afford the title compound in sufficient purity for use in the next step. MS: m/z=411.3 [M+H].

Step B: 4-[(1R,3R)-3-(4,4-Dimethyl-4H-3,1-benzoxazin-2-yl)-2,2-difluorocyclopropyl]benzenesulfonamide A mixture of (1R,3R)-2,2-difluoro-N-[2-(2-hydroxypropan-2-yl)phenyl]-3-(4-sulfamoylphenyl)cyclopropanecarboxamide (37 mg, 0.090 mmol) and polyphosphoric acid (5 mL) was heated at 110° C. for 4 h. The reaction mixture was allowed to cool and was treated with water (5 mL), and the resulting mixture was extracted with ethyl acetate (3×5 mL). The combined organic extracts were dried (magnesium sulfate), filtered, and concentrated under reduced pressure. The residue was purified by silica gel chromatography, eluting with a gradient of ethyl acetate:hexanes—0:100 to 40:60 to afford the title compound. MS: m/z=393.3 [M+H]. $^1$H NMR (500 MHz, CDCl$_3$): δ 7.92 (d, J=8.2 Hz, 2H); 7.46 (d, J=8.0 Hz, 2H); 7.28 (d, J=7.6 Hz, 1H); 7.20 (t, J=7.5 Hz, 1H); 7.16 (d, J=7.7 Hz, 1H), 7.10 (d, J=7.7 Hz, 1H); 4.80 (s, 2H); 3.69-3.65 (m, 1H); 3.02-2.62 (m, 1H); 1.70 (s, 3H); 1.62 (s, 3H).

The examples appearing in the following tables were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE EX-A

| Example | X | Y | R$^1$ | R$^2$ | R$^3$ | R$^4$ | MS [M + H] |
|---|---|---|---|---|---|---|---|
| A1 | Me | O | H | H | H | OMe | 373.1 |
| A2 | H | O | H | F | H | H | 333.2 |
| A3 | Me | S | H | F | H | F | 395.1 |
| A4 | Me | O | H | H | H | H | 343.1 |
| A5 | Me | O | H | Cl | H | H | 377.0 |
| A6 | Me | O | H | H | Cl | H | 377.0 |
| A7 | F | O | H | H | H | H | 351.1 |
| A8 | F | S | H | H | H | H | 367.2 |
| A9 | F | NH | H | H | H | H | 350.1 |

TABLE EX-B

| Example | X | Y | R$^1$ | R$^2$ | R$^3$ | R$^4$ | MS [M + H] |
|---|---|---|---|---|---|---|---|
| B1 | Me | O | H | F | H | F | 379.1 |
| B2 | Me | O | H | F | H | H | 361.1 |
| B3 | Me | S | H | H | H | H | 359.1 |
| B4 | H | O | H | H | H | H | 315.0 |
| B5 | Me | O | H | Cl | H | H | 377.1 |
| B6 | Me | O | H | H | Cl | H | 377.0 |
| B7 | H | O | H | F | H | H | 333.2 |
| B8 | Me | S | H | F | H | F | 395.0 |
| B9 | Me | S | H | F | H | H | 377.1 |
| B10 | Me | O | H | H | OMe | H | 373.1 |
| B11 | F | O | H | H | H | H | 351.2 |
| B12 | F | S | H | H | H | H | 367.1 |

TABLE EX-C

| Example | X | R | MS [M + H] |
|---|---|---|---|
| C1 | Me | 2-quinazolinyl | 354.2 |
| C2 | Me | 6-fluoro-2-quinazolinyl | 372.2 |
| C3 | Me | 4,5,6,7-tetrahydrobenzoxazol-2-yl | 347.2 |
| C4 | F | 4,5,6,7-tetrahydrobenzoxazol-2-yl | 355.2 |

TABLE EX-D

| Example | X | R | MS [M + H] |
|---|---|---|---|
| D1 | Me | 2-quinazolinyl | 354.2 |
| D2 | Me | oxazolo[5,4-b]pyridin-2-yl | 344.1 |
| D3 | Me | 4,5,6,7-tetrahydrobenzoxazol-2-yl | 347.2 |
| D4 | Me | 1-methyl-5,7-difluorobenzimidazol-2-yl | 392.1 |
| D5 | F | 4,4-dimethyl-4H-benzo[d][1,3]oxazin-2-yl | 393.2 |

TABLE EX-E

| Example | Cyclopropyl Stereochemistry | X | R | MS [M + H] |
|---|---|---|---|---|
| E1 | trans, racemic | H | 2-methylbenzothiazol-4-yl | 345.0 |

TABLE EX-E-continued
| Example | Cyclopropyl Stereochemistry | X | R | MS [M + H] |
|---|---|---|---|---|
| E2 | trans, racemic | H | 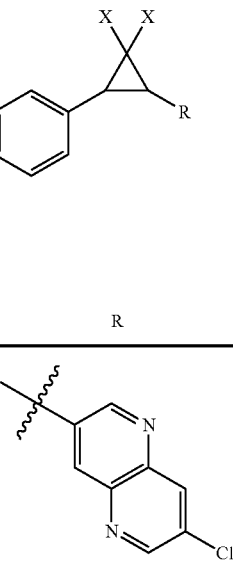 | 360.0 |
| E3 | trans, racemic | H | 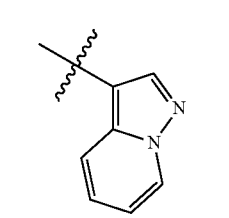 [SMILES: *c1cnn2ccccc12] | 314.1 |
| E4 | trans, racemic | H | 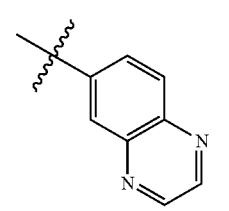 [SMILES: *c1ccc2nccnc2c1] | 326.1 |
| E5 | trans, racemic | H | 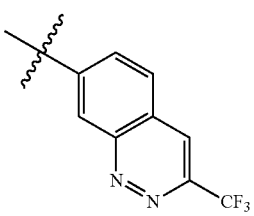 [SMILES: *c1ccc2cc(C(F)(F)F)nnc2c1] | 394.1 |
| E6 | trans, racemic | H | 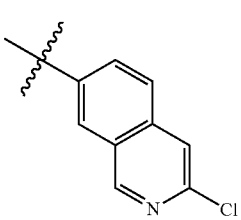 [SMILES: *c1ccc2cc(Cl)ncc2c1] | 359.1 |
| E7 | trans, racemic | H | 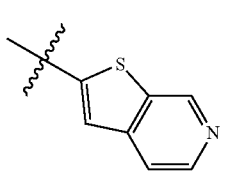 [SMILES: *c1cc2ccncc2s1] | 331.0 |
| E8 | trans, racemic | H | 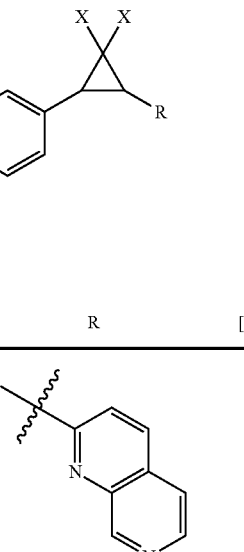 | 326.1 |
| E9 | trans, racemic | H | 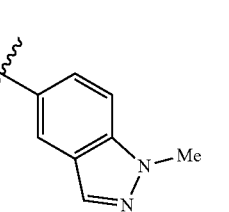 | 328.1 |
| E10 | trans, racemic | H | 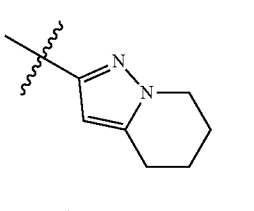 [SMILES: *c1cc2n(n1)CCCC2] | 318.1 |
| E11 | trans, racemic | H | 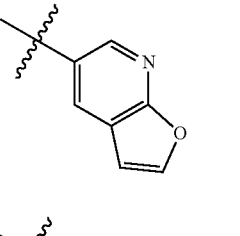 | 315.1 |
| E12 | trans, racemic | H | 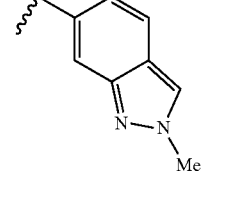 | 328.1 |
| E13 | trans, racemic | H | 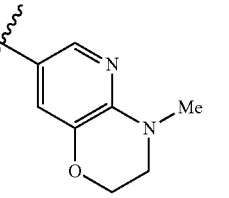 | 346.1 |

TABLE EX-E-continued

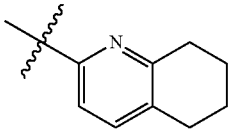 [SMILES: *c1ccc2c(n1)CCCC2]

| Ex- ample | Cyclopropyl Stereo- chemistry | X | R | MS [M + H] |
|---|---|---|---|---|
| E14 | trans, racemic | H | (5,6,7,8-tetrahydroquinolin-2-yl) | 329.1 |

The utility of the compounds in accordance with the present invention as positive allosteric modulators of α7 nicotinic acetylcholine receptor activity may be demonstrated by methodology known in the art. Direct activation of α7 (agonism), and potentiation of acetylcholine-evoked α7 currents was determined as follows:

Automated Patch-Clamp Electrophysiology Functional Assay (Assay A)

Automated patch-clamp electrophysiology was performed using the IonFlux HT (Fluxion Biosciences Inc., San Francisco, Calif.) in the whole-cell, population patch configuration. Test compounds were assessed for their ability to modulate the function of the α7 nicotinic acetylcholine receptor both in the presence, and in the absence of the natural α7 agonist acetylcholine. A HEK cell line stably expressing both human RIC-3 and human α7 (PrecisION hnAChR α7/RIC-3, Eurofins Pharma, St. Charles, Mo.) was cultured in 175 cm² triple-layer tissue culture flasks to no more than 90% confluency in DMEM/F-12 growth media supplemented with 10% heat-inactivated fetal bovine serum, 1% non-essential amino acids, 0.625 µg/mL Puromycin, and 400 µg/mL Geneticin. Immediately prior to assay, cells were detached by first aspirating growth media, rinsing with Dulbecco's phosphate buffered saline, and then adding 10 mL of Accutase (Innovative Cell Technologies, San Diego, Calif.) to the flask and then incubating at 37° C. for 5 minutes. Detached cells were then recovered by the addition of 40 mL of CHO-serum-free media supplemented with 25 mM HEPES, and rocked gently in a 50 mL conical tube for 20 minutes prior to patch-clamp assay. After recovery, cells were pelleted by centrifugation at 1,000 RPM for 1 minute in a compact bench top centrifuge; recovery media was aspirated and cells were resuspended in external recording solution (150 mM NaCl, 5 mM KCl, 2 mM $CaCl_2$, 1 mM $MgCl_2$, 10 mM HEPES, 12 mM dextrose) to a density of $5.0 \times 10^6$ cells/mL. The cell suspension was added to the cell inlet wells on an IonFlux HT population patch plate which had previously been rinsed and primed with deionized $H_2O$. Test compounds were serially diluted in DMSO and then resuspended to the final test concentration in external recording solution, with, or without 40 µM acetylcholine added to the external recording solution; test compounds were then transferred to the IonFlux HT population patch plate. Internal recording solution (110 mM $TrisPO_4$, 28 mM TrisBase, 0.1 mM $CaCl_2$, 2 mM $MgCl_2$, 11 mM EGTA, 4 mM MgATP) was added to the internal recording solution inlet wells on the IonFlux HT patch plate previously loaded with cells and test compounds, and the plate loaded into the IonFlux HT instrument. A protocol was executed on the IonFlux HT to trap the cells, break into the cells, and establish the whole-cell recording configuration; cells were voltage-clamped at a holding potential of −60 mV for the duration of the experiment, all experiments were conducted at room temperature, and the IonFlux HT injection pressure was 8 psi for solution applications. Upon establishing the whole-cell configuration, external recording solution was perfused into the recording chambers for 120 seconds and then 40 µM acetylcholine was applied for 1 second and immediately washed off with external recording solution for 60 seconds. The 40 µM acetylcholine-evoked α7 current served as the current response to which subsequent test compound effects, in the presence, or in the absence of 40 µM acetylcholine would be quantified relative to. Next, test compounds were evaluated at multiple concentrations for their ability to induce, or modulate α7 current responses; three concentrations of test compound were evaluated in ascending dose fashion per recording. To assess test compound agonist activity, test compound diluted in external recording solution was applied starting from the lowest concentration of test compound being tested in the concentration series, for 58 seconds; the first 20 seconds of the 58 second compound application period coincided with a data collection sweep which was 20 seconds in duration, and collected at a rate of 5,000 samples/second. To assess test compound positive allosteric modulator activity, immediately following the 58 second test compound only application period, the same concentration of test compound, diluted in external recording solution containing 40 µM acetylcholine was applied for 1 second; in this way, the test compound and the natural receptor agonist acetylcholine were co-applied, and potentiating effects of test compounds observed. The 1 second application of test compound diluted in external solution containing 40 µM acetylcholine coincided with a data collection sweep which was 20 seconds in duration, and collected at a rate of 5,000 samples/second, after which, external recording solution only was applied for 42 seconds. Following this 42 second wash with external recording solution only, the next highest concentration of the test compound in the concentration series was applied in the absence and then in the presence of acetylcholine as previously described, and data collected as previously described. After test compound agonist, and positive allosteric modulator activity were assessed at three ascending concentrations, the experiment was terminated and leak subtraction performed using the IonFlux HT data analysis software. Peak current amplitudes and the area under the curve (AUC) were both quantified for each current sweep using proprietary software and test compound effects where quantified as follows.

Test compound agonist activity was calculated as:

$$\% \text{ Agonism} = (Y/X) \times 100$$

Test compound potentiator activity was calculated as:

$$\% \text{ Potentiation} = [(Z/X) \times 100] - 100$$

X=Peak current amplitude (or AUC) evoked by 40 µM acetylcholine
Y=Peak current amplitude (or AUC) evoked by test compound diluted in external recording solution Z=Peak current amplitude (or AUC) evoked by test compound diluted in external recording solution containing 40 μM acetylcholine As such, test compounds which evoked the same current amplitude as 40 μM acetylcholine alone would exhibit a calculated % Agonism of 100%. Test compounds co-applied with 40 μM acetylcholine which evoked a current amplitude 2× the current evoked from 40 μM acetylcholine alone would exhibit a calculated % Potentiation of 100%, whereas test compounds co-applied with 40 μM acetylcholine which evoked the same current amplitude as 40 μM acetylcholine alone would be characterized as exhibiting no potentiation.

Agonist and potentiation data, derived by peak current amplitude or area under the curve (AUC) were graphed and fit using a 4-parameter logistic fit based on the Levenberg-Marquardt algorithm where $y=A+((B-A)/(1+((C/x)^D)))$ where:
A=Minimum
B=Maximum
C=$EC_{50}$
D=Slope
x=test compound concentration
y=% Agonism or % Potentiation Potency data for selected compounds of the present invention in the automated patch-clamp electrophysiology functional assay (Assay A) are represented in the table below:

| Example | α7 nAChR Potency |
|---|---|
| 1 | C |
| 2 | A |
| 3 | B |
| 4 | C |
| 5 | B |
| 6 | C |
| 7 | C |
| 8 | C |
| 9 | B |
| 10 | B |
| 11 | C |
| 12 | C |
| 13 | C |
| A1 | C |
| A2 | A |
| A3 | C |
| A4 | B |
| A5 | C |
| A6 | B |
| A7 | A |
| A8 | A |
| A9 | C |
| B1 | B |
| B2 | B |
| B3 | C |
| B4 | C |
| B5 | B |
| B6 | B |
| B7 | C |
| B8 | B |
| B9 | B |
| B10 | C |
| B11 | B |
| B12 | B |
| C1 | C |
| C2 | C |
| C3 | B |
| C4 | C |
| D1 | D |
| D2 | C |
| D3 | C |
| D4 | D |
| D5 | C |
| E1 | B |
| E2 | C |
| E3 | C |
| E4 | C |
| E5 | C |
| E6 | C |
| E7 | C |
| E8 | C |
| E9 | C |
| E10 | D |
| E11 | C |
| E12 | C |
| E13 | C |
| E14 | C |

*Potency defined as A ($EC_{50} \leq 0.1$ μM); B (0.1 μM < $EC_{50} \leq 0.5$ μM); C (0.5 μM < $EC_{50} \leq 5$ μM); D (5 μM < $EC_{50} \leq 50$ μM)

Electrophysiology $EC_{50}$ values for selected compounds of the present invention in the automated patch-clamp electrophysiology functional assay (Assay A) are provided in the table below:

| Example | α7 nAChR $EC_{50}$ (nM) |
|---|---|
| 1 | 620 |
| 2 | 71 |
| 3 | 370 |
| 4 | 610 |
| 5 | 160 |
| 6 | 3400 |
| 7 | 1300 |
| 8 | 3800 |
| 9 | 350 |
| 10 | 450 |
| 11 | 2000 |
| 12 | 2500 |
| 13 | 1800 |
| A1 | 830 |
| A2 | 60 |
| A3 | 960 |
| A4 | 280 |
| A5 | 1200 |
| A6 | 430 |
| A7 | 52 |
| A8 | 38 |
| B2 | 300 |
| B3 | 3400 |
| B6 | 200 |
| B7 | 4200 |
| B9 | 170 |
| B10 | 660 |
| B11 | 430 |
| C1 | 1400 |
| C3 | 120 |
| D1 | 7200 |
| D2 | 3400 |
| D5 | 1100 |
| E1 | 410 |
| E3 | 3500 |
| E6 | 1200 |
| E9 | 2800 |
| E12 | 5000 |
| E13 | 880 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula I:

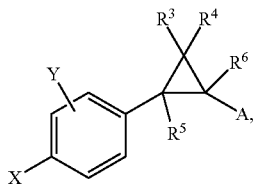
(I)

or a pharmaceutically acceptable salt thereof, wherein:
X is selected from

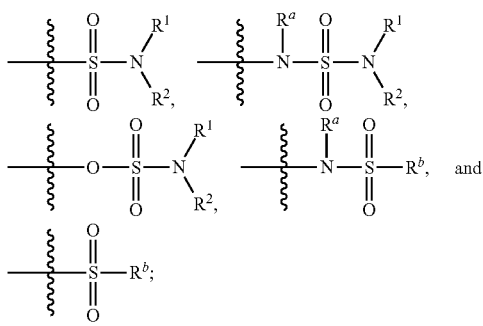

Y is 4 substituents, each independently selected from H, $(C_1\text{-}C_4)$alkyl, halogen, and OH, wherein said alkyl is optionally substituted with one or more halogen or OH;

A is a bicyclic heteroaryl ring which is substituted with 0 to 4 R groups each independently selected from OH, oxo, amino, amido, carboxyl, keto, CN, alkoxy, $S(O)_m$-alkyl, halogen, aminoalkyl, hydroxyalkyl, alkyl, cycloalkyl, alkynyl, aryl, heteroaryl, and heterocyclyl, wherein said amino, amido, carboxyl, keto, alkoxy, $S(O)_m$-alkyl, aminoalkyl, hydroxyalkyl, alkyl, cycloalkyl, alkynyl, aryl, heteroaryl and heterocyclyl are optionally substituted with one or more substituents independently selected from F, Cl, Br, OH, oxo, $CF_3$, $OCF_3$, CN, $(C_1\text{-}C_6)$alkyl, $O(C_1\text{-}C_4)$alkyl, $S(O)_m$—$(C_1\text{-}C_4)$alkyl, C=$O(C_1\text{-}C_4)$alkyl, (C=O)$NR^7R^8$, (C=O)$OR^7$, $(C_2\text{-}C_4)$alkynyl, $(C_3\text{-}C_6)$cycloalkyl, $O(C_3\text{-}C_6)$cycloalkyl, C=$O(C_3\text{-}C_6)$cycloalkyl, aryl, heteroaryl and heterocyclyl, wherein said alkyl, aryl, heteroaryl and heterocyclyl are optionally independently substituted with one or more halogen, $CF_3$, OH and oxo;

$R^1$ is H or $(C_1\text{-}C_4)$alkyl;
$R^2$ is H or $(C_1\text{-}C_4)$alkyl;
$R^3$ is H, halogen or $(C_1\text{-}C_4)$alkyl, wherein said alkyl is optionally substituted with one or more halogen;
$R^4$ is H, halogen or $(C_1\text{-}C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1\text{-}C_4)$alkyl;
$R^5$ is H or $(C_1\text{-}C_4)$alkyl;
$R^6$ is H or $(C_1\text{-}C_4)$alkyl;
$R^7$ is H or $(C_1\text{-}C_4)$alkyl, wherein said alkyl is optionally substituted with one or more halogen;
$R^8$ is H or $(C_1\text{-}C_4)$alkyl, wherein said alkyl is optionally substituted with one or more halogen;
$R^a$ is H or $(C_1\text{-}C_4)$alkyl;
$R^b$ is H or $(C_1\text{-}C_4)$alkyl; and
m is 0, 1, or 2.

2. The compound of claim 1, or a pharmaceutically acceptable salt thereof, wherein X is

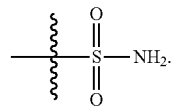

3. The compound according to claim 2, or a pharmaceutically acceptable salt thereof, wherein Y is H.

4. The compound of according to claim 3, or a pharmaceutically acceptable salt thereof, wherein A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl, dihydropyridooxazinyl, tetrahydrobenzothiazolyl, tetrahydroquinazolinyl, benzoxazinyl, benzimidazolyl, thiazolopyridinyl, quinolinyl, pyridopyrimidinyl, phthalazinyl, pyridopyrazinyl, thienoxazole, and thienothiazole each optionally substituted with 1 to 2 R groups independently selected from halogen, CN, $(C_1\text{-}C_6)$alkyl, $O(C_1\text{-}C_6)$alkyl, $NR^7R^8$, $(C_3\text{-}C_6)$cycloalkyl, aryl, heteroaryl and heterocyclyl, wherein said alkyl, $NR^7R^8$, $(C_3\text{-}C_6)$cycloalkyl, aryl, heteroaryl and heterocyclyl are each optionally substituted with one or more substituents independently selected from halogen, CN, $(C_1\text{-}C_6)$alkyl, (C=O)$O(C_1\text{-}C_4)$alkyl, and phenyl.

5. The compound according to claim 4, or a pharmaceutically acceptable salt thereof, wherein $R^5$, $R^6$, $R^a$ and $R^b$ are independently H or methyl.

6. The compound according to claim 5, or a pharmaceutically acceptable salt thereof, wherein $R^3$ and $R^4$ are independently H, F or methyl.

7. The compound of claim 1, or a pharmaceutically acceptable salt thereof, having the formula:

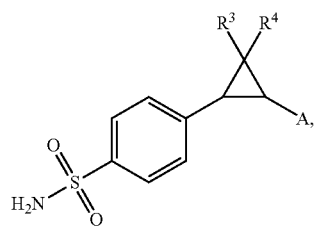
(Ia)

or a pharmaceutically acceptable salt thereof, wherein;
A is selected from benzoxazolyl, quinazolinyl, tetrahydrobenzoxazolyl, oxazolopyridinyl, quinoxalinyl, imidazopyridazinyl, benzothiazolyl, dihydrocyclopentaoxazolyl, naphthyridinyl, pyrazolopyridinyl, cinnolinyl, isoquinolyl, thienopyridinyl, indazolyl, tetrahydropyrazolopyridinyl, furopyridinyl and dihydropyridooxazinyl, each optionally substituted with 1 to 2 R groups independently selected from F, Cl, $(C_1\text{-}C_4)$alkyl, $O(C_1\text{-}C_4)$alkyl and $CF_3$;

R³ is H, F or methyl; and
R⁴ is H, F or methyl.

8. The compound of claim 1 which is selected from the group consisting of

4-[(1R,3R)-3-(1,3-Benzoxazol-2-yl)-2,2-dimethylcyclopropyl]benzenesulfonamide;
4-[(1S,3S)-3-(6-Fluoro-1,3-benzoxazol-2-yl)-2,2-dimethylcyclopropyl]benzenesulfonamide;
4-[(1R,2R)-2-(Quinazolin-2-yl)cyclopropyl]benzenesulfonamide;
4-[(1R,2R)-2-(4,5,6,7-Tetrahydro-1,3-benzoxazol-2-yl)cyclopropyl]benzenesulfonamide;
4-[(1R,2R)-2-(1,3-Benzoxazol-2-yl)cyclopropyl]benzenesulfonamide;
4-[(1R,3R)-2,2-Dimethyl-3-([1,3]oxazolo[5,4-b]pyridin-2-yl)cyclopropyl]benzenesulfonamide;
4-[trans-2-(Quinoxalin-2-yl)cyclopropyl]benzenesulfonamide;
4-((1R,3R)-3-(Imidazo[1,2-b]pyridazin-2-yl)-2,2-dimethylcyclopropyl)benzenesulfonamide;
4-((1S,3S)-3-(Benzo[d]thiazol-2-yl)-2,2-dimethylcyclopropyl)benzenesulfonamide;
4-((1S,3S)-3-(6-Fluorobenzo[d]thiazol-2-yl)-2,2-dimethylcyclopropyl)benzenesulfonamide;
4-[(1R,3R)-3-(5,6-Dihydro-4H-cyclopenta[d][1,3]oxazol-2-yl)-2,2-dimethylcyclopropyl] benzenesulfonamide;
4-[(1R,3R)-2,2-Dimethyl-3-(5,6,7,8-tetrahydroquinazolin-2-yl)cyclopropyl]benzenesulfonamide;
4-[(1R,3R)-3-(4,4-Dimethyl-4H-3,1-benzoxazin-2-yl)-2,2-difluorocyclopropyl]benzenesulfonamide;
4-[(1S,3S)-3-(4-Methoxy-1,3-benzoxazol-2-yl)-2,2-dimethyl-cyclopropyl]benzenesulfonamide;
4-[(1R,2R)-2-(6-Fluoro-1,3-benzoxazol-2-yl)cyclopropyl]benzenesulfonamide;
4-[(1S,3S)-3-(4,6-Difluoro-1,3-benzothiazol-2-yl)-2,2-dimethyl-cyclopropyl] benzenesulfonamide;
4-[(1S,3S)-3-(1,3-Benzoxazol-2-yl)-2,2-dimethyl-cyclopropyl]benzenesulfonamide;
4-[(1S,3S)-3-(6-Chloro-1,3-benzoxazol-2-yl)-2,2-dimethyl-cyclopropyl]benzenesulfonamide;
4-[(1S,3S)-3-(5-Chloro-1,3-benzoxazol-2-yl)-2,2-dimethyl-cyclopropyl]benzenesulfonamide;
4-[(1R,3R)-3-(1,3-Benzoxazol-2-yl)-2,2-difluoro-cyclopropyl]benzenesulfonamide;
4-[(1R,3S)-3-(1,3-Benzothiazol-2-yl)-2,2-difluoro-cyclopropyl]benzenesulfonamide;
4-[(1R,3R)-3-(1H-Benzimidazol-2-yl)-2,2-difluorocyclopropyl]benzenesulfonamide;
4-[(1R,3R)-3-(4,6-Difluoro-1,3-benzoxazol-2-yl)-2,2-dimethyl-cyclopropyl]benzenesulfonamide;
4-[(1R,3R)-3-(6-Fluoro-1,3-benzoxazol-2-yl)-2,2-dimethyl-cyclopropyl]benzenesulfonamide;
4-[(1R,3R)-3-(1,3-Benzothiazol-2-yl)-2,2-dimethyl-cyclopropyl]benzenesulfonamide;
4-[(1S,2S)-2-(1,3-Benzoxazol-2-yl)cyclopropyl]benzenesulfonamide;
4-[(1R,3R)-3-(6-Chloro-1,3-benzoxazol-2-yl)-2,2-dimethyl-cyclopropyl]benzenesulfonamide;
4-[(1R,3R)-3-(5-Chloro-1,3-benzoxazol-2-yl)-2,2-dimethyl-cyclopropyl]benzenesulfonamide;
4-[(1S,2S)-2-(6-Fluoro-1,3-benzoxazol-2-yl)cyclopropyl]benzenesulfonamide;
4-[(1R,3R)-3-(4,6-Difluoro-1,3-benzothiazol-2-yl)-2,2-dimethyl-cyclopropyl] benzenesulfonamide;
4-[(1R,3R)-3-(6-Fluoro-1,3-benzothiazol-2-yl)-2,2-dimethyl-cyclopropyl]benzenesulfonamide;
4-[(1R,3R)-3-(5-Methoxy-1,3-benzoxazol-2-yl)-2,2-dimethyl-cyclopropyl]benzenesulfonamide;
4-[(1S,3S)-3-(1,3-Benzoxazol-2-yl)-2,2-difluoro-cyclopropyl]benzenesulfonamide;
4-[(1S,3R)-3-(1,3-Benzothiazol-2-yl)-2,2-difluoro-cyclopropyl]benzenesulfonamide;
4-[(1S,3S)-2,2-Dimethyl-3-quinazolin-2-yl-cyclopropyl]benzenesulfonamide;
4-[(1S,3S)-3-(5-Fluoroquinazolin-2-yl)-2,2-dimethyl-cyclopropyl]benzenesulfonamide;
4-[(1S,3S)-2,2-Dimethyl-3-(4,5,6,7-tetrahydro-1,3-benzoxazol-2-yl)cyclopropyl] benzenesulfonamide;
4-[(1R,3R)-2,2-Difluoro-3-(4,5,6,7-tetrahydro-1,3-benzoxazol-2-yl)cyclopropyl] benzenesulfonamide;
4-[(1R,3R)-2,2-Dimethyl-3-quinazolin-2-yl-cyclopropyl] benzenesulfonamide;
4-[(1R,3R)-2,2-Dimethyl-3-oxazolo[5,4-c]pyridin-2-yl-cyclopropyl]benzenesulfonamide;
4-[(1R,3R)-2,2-Dimethyl-3-(4,5,6,7-tetrahydro-1,3-benzoxazol-2-yl)cyclopropyl] benzenesulfonamide;
4-[(1R,3R)-3-(5,7-Difluoro-1-methyl-benzimidazol-2-yl)-2,2-dimethyl-cyclopropyl] benzenesulfonamide;
4-[(1S,3S)-3-(4,4-Dimethyl-4H-3,1-benzoxazin-2-yl)-2,2-difluorocyclopropyl]benzenesulfonamide;
4-[2-(2-Methyl-1,3-benzothiazol-4-yl)cyclopropyl]benzenesulfonamide;
4-[2-(7-Chloro-1,5-naphthyridin-3-yl)cyclopropyl]benzenesulfonamide;
4-(2-Pyrazolo[1,5-a]pyridin-3-ylcyclopropyl)benzenesulfonamide;
4-(2-Quinoxalin-6-ylcyclopropyl)benzenesulfonamide;
4-[2-[3-(Trifluoromethyl)cinnolin-7-yl] cyclopropyl]benzenesulfonamide;
4-[2-(3-Chloro-7-isoquinolyl)cyclopropyl]benzenesulfonamide;
4-(2-Thieno[2,3-c]pyridin-2-ylcyclopropyl)benzenesulfonamide;
4-[2-(1,7-Naphthyridin-2-yl)cyclopropyl]benzenesulfonamide;
4-[2-(1-Methylindazol-5-yl)cyclopropyl]benzenesulfonamide;
4-[2-(4,5,6,7-Tetrahydropyrazolo[1,5-a]pyridin-2-yl)cyclopropyl]benzenesulfonamide;
4-(2-Furo[2,3-b]pyridin-5-ylcyclopropyl)benzenesulfonamide;
4-[2-(2-Methylindazol-6-yl)cyclopropyl]benzenesulfonamide;
4-[2-(4-Methyl-2,3-dihydropyrido[3,2-b][1,4]oxazin-7-yl)cyclopropyl]benzenesulfonamide; and
4-[2-(5,6,7,8-Tetrahydroquinolin-3-yl)cyclopropyl]benzenesulfonamide;

or a pharmaceutically acceptable salt thereof.

9. A pharmaceutical composition comprising (i) a pharmaceutically acceptable carrier and (ii) a compound according to claim 1 or a pharmaceutically acceptable salt thereof.

10. The pharmaceutical composition of claim 9, further comprising a second therapeutic agent selected from the group consisting of acetylcholinesterase inhibitors; NMDA receptor antagonists; antipsychotics; MAO-B inhibitors; and levodopa.

11. A method of treating a patient with cognitive impairments associated with Alzheimer's disease, Parkinson's disease, and schizophrenia, the method comprising administering to the patient the compound according to claim 1, or a pharmaceutically acceptable salt thereof, in an amount effective to treat the patient.

12. A method of modulating α7 nAChR activity in a mammal comprising administering to the mammal an effective amount of compound according to claim 1 or a pharmaceutically acceptable salt thereof.

13. A method of treating a patient with mild to moderate dementia of the Alzheimer's type, the method comprising administering to the patient the compound according to claim 1 or a pharmaceutically acceptable salt thereof, in an amount effective to treat the patient.

* * * * *